(12) United States Patent
Lewis et al.

(10) Patent No.: US 7,064,174 B2
(45) Date of Patent: *Jun. 20, 2006

(54) SILICON CONTAINING COMPOUNDS

(75) Inventors: Andrew Lennard Lewis, Surrey (GB); Anthony Claude Marie Collias, Surrey (GB); Richard Paul Redman, Surrey (GB); Jane Louise Court, Surrey (GB); Sean Leo Willis, Surrey (GB)

(73) Assignee: Biocompatibles UK Limited, Surrey (GB)

( * ) Notice: Subject to any disclaimer, the term of this patent is extended or adjusted under 35 U.S.C. 154(b) by 265 days.

This patent is subject to a terminal disclaimer.

(21) Appl. No.: 10/203,203

(22) PCT Filed: Feb. 7, 2001

(86) PCT No.: PCT/GB01/00519

§ 371 (c)(1),
(2), (4) Date: Oct. 9, 2002

(87) PCT Pub. No.: WO01/57048

PCT Pub. Date: Aug. 9, 2001

(65) Prior Publication Data

US 2003/0152786 A1 Aug. 14, 2003

(30) Foreign Application Priority Data

Feb. 7, 2000 (EP) .................................. 00300942

(51) Int. Cl.
*C08G 77/26* (2006.01)
(52) U.S. Cl. .............................. 528/38; 528/26; 528/28; 528/30; 526/279; 556/405; 556/425; 556/418
(58) Field of Classification Search .................. 528/28, 528/26, 30, 38; 526/279, 425, 405, 418
See application file for complete search history.

(56) References Cited

U.S. PATENT DOCUMENTS

| | | |
|---|---|---|
| 2,924,588 A | 9/1960 | Speier |
| 3,146,250 A | 8/1964 | Speier |
| 4,348,329 A | 9/1982 | Chapman |
| 4,603,086 A | 7/1986 | Fujii et al. |
| 4,606,933 A * | 8/1986 | Griswold et al. ............ 427/515 |
| 4,654,161 A | 3/1987 | Kollmeier et al. |
| 4,734,475 A | 3/1988 | Goldenberg et al. |
| 4,780,515 A | 10/1988 | Deichert |
| 4,789,710 A * | 12/1988 | Furukawa et al. ........... 525/440 |
| 4,912,240 A | 3/1990 | Owen et al. |
| 4,962,178 A | 10/1990 | Harisiades |
| 5,010,141 A | 4/1991 | Mueller |
| 5,070,169 A | 12/1991 | Robertson et al. |
| 5,194,251 A | 3/1993 | Halloran et al. |
| 5,321,108 A | 6/1994 | Kunzler et al. |
| 5,352,714 A | 10/1994 | Lai et al. |
| 5,380,904 A | 1/1995 | Chapman et al. |
| 5,405,983 A | 4/1995 | Fost et al. |

(Continued)

FOREIGN PATENT DOCUMENTS

EP 0 109 355 B1 5/1984

(Continued)

OTHER PUBLICATIONS

D.C. Cole, "Recent Stereoselective Synthetic Approaches to -amino acids," *Tetrahedron*, vol. 50, No. 32, pp. 9528-41.

(Continued)

*Primary Examiner*—Margaret G. Moore
(74) *Attorney, Agent, or Firm*—Sughrue Mion, PLLC

(57) ABSTRACT

A silicon containing adduct having the formula (I) wherein X is an electron withdrawing group selected from the group consisting of carbonyl and sulphone groups, sulphonium and phosphonium salts; R is selected from the group consisting of hydrogen, linear and branched alkyl, alkenyl, alkynyl, cycloalkyl, cycloalkenyl, cycloalkynyl, aryl, alkaryl, aralkyl, alkoxyaryl, alkoxyalkyl, oligoalkoxyalkyl, di-alkylaminoalkyl, N-aryl-N-alky-laminoalkyl, hydroxyalkoxy, alkoxy, alkenyloxy, alkynyloxy, cycloalkoxy, cycloalkenyloxy, cycloalkynyloxy, aralkoxy, alkoxyaryloxy, alkoxyalkoxy, oligoalkoxyalkoxy, di-alkylaminoalkoxy, N-aryl-N-alkylamino-alkoxy, acyloxy, acyloxyalkyl, N-diacyliminoalkyl groups, organosilane, organosiloxane, hydroxyaryl, hydroxyalkenyl, hydroxyalkynyl and hydroxy groups and any of the above groups substituted with one or more hydroxyl or xzwitterionic group Z, or R—X— is a nitrile group; $R^3$ and $R^4$ are individually selected from the group consisting of hydrogen, linear and branched alkyl, alkenyl, and alkynyl groups, aryl, alkoxycarbonyl, alkylaminocarbonyl, cycloalkyl, cycloalkenyl, cycloalkynyl, haloaryl, haloalkyl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, alkylaminocarbonyl, oxacycloalkyl, oxacycloalkenyl, organosilane and organosiloxane groups and any of the above groups substituted with a zwitterionic group Z, a hydroxyl group or an isocyanate group; $R^1$ and $R^2$ are individually selected from hydrogen and $C_{1-12}$ alkyl groups; and at least one of groups R, $R^3$, and $R^4$ contain an organosiloxane group Y and/or an organosilane group U. The invention additionally provides processes for the production of such an adduct, polymers formed therefrom, coating processes and compositions comprising an adduct or polymers produced therefrom

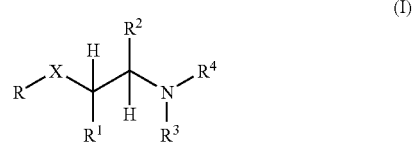

(I)

29 Claims, 1 Drawing Sheet

U.S. PATENT DOCUMENTS

| | | | |
|---|---|---|---|
| 5,451,617 A | 9/1995 | Lai et al. | |
| 5,453,467 A | 9/1995 | Bamford et al. | |
| 5,486,579 A | 1/1996 | Lai et al. | |
| 5,550,219 A | 8/1996 | O'Lenick, Jr. | |
| 5,556,710 A | 9/1996 | Russell et al. | |
| 5,602,224 A | 2/1997 | Vrckovnik et al. | |
| 5,645,883 A | 7/1997 | Russell et al. | |
| 5,648,442 A | 7/1997 | Bowers et al. | |
| 5,712,327 A | 1/1998 | Chang et al. | |
| 5,717,047 A | 2/1998 | Russell et al. | |
| 5,760,100 A | 6/1998 | Nicolson et al. | |
| 5,786,086 A | 7/1998 | Frihart et al. | |
| 5,792,827 A | 8/1998 | Hintze-Bruning et al. | |
| 6,177,511 B1 * | 1/2001 | Dauth et al. | 524/838 |
| 6,420,453 B1 | 7/2002 | Bowers et al. | |

FOREIGN PATENT DOCUMENTS

| | | |
|---|---|---|
| EP | 0 188 895 A1 | 7/1986 |
| EP | 0 230 342 A2 | 7/1987 |
| EP | 0 276 114 A2 | 7/1988 |
| EP | 0 400 827 A2 | 12/1990 |
| EP | 0 455 585 A1 | 11/1991 |
| EP | 0 611 379 B1 | 8/1994 |
| EP | 0 713 894 A2 | 5/1996 |
| EP | 0 818 479 A2 | 1/1998 |
| EP | 0 844 268 A1 | 5/1998 |
| EP | 0 899 287 A1 | 3/1999 |
| EP | 0 933 399 A1 | 8/1999 |
| JP | 09291135 | 11/1977 |
| WO | WO 84/02705 | 7/1984 |
| WO | WO 93/09154 | 5/1993 |
| WO | WO 93/09155 | 5/1993 |
| WO | WO 93/12870 | 7/1993 |

OTHER PUBLICATIONS

Michael T. Nowak, "High solids coatings-formulation aspects," *High Solids Coat.*, (Sep. 1982) vol. 7, No. 3, pp. 23-28.

Kwiatkowski et al., "A Synthesis of N-Substituted β-Alanines: Michael Addition of Amines to Trimethylsilyl Acrylate," *Synthesis*, (Dec. 1989), issue 12, pp. 946, 949.

Cabral et al., "Catalysis of the specific Michael Addition: the example of acrylate acceptors," *Tetrahedron Lett.*, vol. 30, No. 30, (1989), pp. 3969-3972.

* cited by examiner

SILICON CONTAINING COMPOUNDS

It is well known in the literature that amines undertake nucleophilic attack on the α,β-unsaturated carbonyl of an acrylate functionality, resulting in a Michael-type 1,4-adduct (Recent stereoselective synthetic approaches to -amino acids. Cole, Derek C., *Tetrahedron* (1994), 50(32), 9517–82).

This technology has been applied in the preparation of a range of curable coatings (Addition products, radiation-curable surface coating compositions based on the addition products, and their use for wood coating and paper coating, Hintze-Bruning, Horst; Cibura, Klaus; Baltus, Wolfgang, U.S. Pat. No. 5,792,827; High-solids coatings—formulation aspects. Nowak, Michael T. USA. *High Solids Coat.* (1982), 7(3), 23–8) or resins (Curing agents for liquid epoxy resins, and curable polymer compositions containing them. Shiono, Kenji; Suzuki, Takehiro. JP 09291135; A process for preparation of room-temperature-curable resins. Furukawa, Hisao; Kawamura, Jo., EP 274112).

It has also been used extensively in polymer science, for example, to produce a variety of polymer hybrids (Conductive wire coating based on a curable acrylate-modified amine-terminated polyamide. Frihart, Charles R.; Kliwinski, Joseph. WO 9724191; A polylactone having amino groups, its preparation, and coating and printing ink compositions containing it. Matsui, Hideki., EP 713894; Grafting of amine-functional polymers onto functionalized oxymethylene polymers and the resulting graft polymers thereof. Auerbach, Andrew B.; Broussard, Jerry A.; Yang, Nan L.; Paul, James L. EP 400827) or to build dendrimer structures (Dense star polymers. Tomalia, Donald A.; Dewald, James R. WO 8402705).

It can also be used to functionalise biologically active amine-bearing compounds (A synthesis of N-substituted -alanines: Michael addition of amines to trimethylsilyl acrylate. Kwiatkowski, Stefan; Jeganathan, Azhwarsamy; Tobin, Thomas; Watt, David S. Maxwell H. *Synthesis* (1989), Issue 12, 946–9).

The reaction may be carried out with either acrylate or methacrylate, although the former is generally preferred in the literature on reactivity grounds. The reaction proceeds usually without catalysis, although there are reports of catalysts to promote soley 1,4 addition in good yields (Catalysis of the specific Michael addition: the example of acrylate acceptors. Cabral, Jose; Laszlo, Pierre; Mahe, Loic; Montaufier, Marie Therese; Randriamahefa, S. Lalatiana., *Tetrahedron Lett*. (1989), 30(30), 3969–72).

In EP-A-0230342 acrylic functional silicone compounds are synthesised by reaction of amine functional silicones with diacrylate compounds. To prevent both acrylate groups of the diacrylate reacting to crosslink the silicone, a monomeric acrylate or an anhydride is added to block further reaction of the diacrylate with amine groups having reactive hydrogen atoms. Other disclosures of using diacrylates to crosslink aminefunctional silicones are made in EP-A-0933399, in which monomeric methacrylates including zwitterionic compounds may also be reacted with amine groups.

Silicone prepolymers have been used in the production of extended wear contact lenses, in processes in which they are copolymerised with hydrophilic and hydrophobic comonomers, with cross-linking agent, to give lenses which are very oxygen permeable, for instance in U.S. Pat. No. 5,760,100. The silicone prepolymers generally comprise sequentially linearly linked siloxane blocks, hydrophilic blocks and ethylenic blocks, with a variety of linking moieties. In EP-A-0455585 ethylenic unsaturation is introduced into amine functional silicones by reaction of the silicone with an isocyanate-functional ethylenic compound.

Phospholipids are phosphate diester compounds, naturally found in the cell membrane, in which one of the alcohol residues is generally a glycerol derivative, and the other is a derivative of a different alcohol which may include a non-ionic, cationic or even an anionic functionality. Phospholipid and phospholipid analogues are of increasing interest, for example to impart the useful properties of biocompatibility, haemocompatibility and to influence the interaction of surfaces with biomolecules such as proteins or enzymes.

Our previous disclosures such as EP-A-0032622, EP-A-0157469, EP-A-0555295, EP-A-0601041, EP-A-0593561, EP-A-00639989, WO-A-9416748 and WO-A-9416749 describe various synthetic zwitterionic compounds including phospholipid analogues and their application in devices having biocompatible and haemocompatible surfaces.

In particular, the present invention relates to new polymers, processes for producing them, processes for coating surfaces with them and polymer compositions. The invention also provides new prepolymers and processes for their production.

Such polymers are particularly useful in the manufacture or coating of devices with medical applications such as blood contacting devices, contact and intraocular lenses, and other devices which are used in contact with protein-containing or biological fluids.

The design of materials for biological or medical applications necessitates that a number of strict material requirements be met. For example, the design of contact lenses necessitates that the material must be optically transparent even after autoclaving, possess chemical stability, have suitable mechanical properties (low modulus of elasticity for patient comfort, adequate tear strength for handling), be biocompatible and have a sufficient water content so that the lens is wettable by tears and moves freely over the eye. In addition, because of lack of blood vesicles in cornea, the lens must be permeable to oxygen directly from the atmosphere. It is also important that the material can be polymerised using present contact lens manufacturing techniques. This normally involves the free radical initiated casting of methacrylate functional monomers, particularly hydrophilic monomers, to form water-swellable hydrogels. These many and often contradictory requirements have most conveniently been met using materials containing, for example, polydimethylsiloxane (PDMS) and polyether compounds.

Polydimethylsiloxane based materials are well known to have low modulus of elasticity, excellent transparency and high oxygen permeability. However, PDMS is completely non wettable by tears and exhibits are high affinity for lipids with poor wetting and lens adhesion. Simple blending of PDMS or methacrylate functionalised PDMS with hydrophilic monomers tends to give rise to incompatibility and phase-separated opaque materials exhibiting poor mechanical properties.

The present invention provides a silicon containing Michael-type adduct having the formula (I)

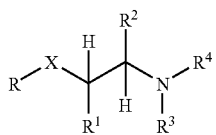
(I)

wherein

X is an electron withdrawing group selected from the group consisting of carbonyl and sulphone groups, sulphonium and phosphonium salts;

R is selected from the group consisting of hydrogen, linear and branched alkyl, alkenyl, alkynyl, cycloalkyl, cycloalkenyl, cycloalkynyl, aryl, alkaryl, aralkyl, alkoxyaryl, alkoxyalkyl, oligoalkoxyalkyl, di-alkylaminoalkyl, N-aryl-N-alkylaminoalkyl, hydroxyalkoxy, alkoxy, alkenyloxy, alkynyloxy, cycloalkoxy, cycloalkenyloxy, cycloalkynyloxy, aralkoxy, alkoxyaryloxy, alkoxyalkoxy, oligoalkoxyalkoxy, di-alkylaminoalkoxy, N-aryl-N-alkylamino-alkoxy, acyloxy, acyloxyalkyl, N-diacyl-iminoalkyl groups, organosilane, organosiloxane, hydroxyaryl, hydroxyalkenyl, hydroxyalkynyl and hydroxy groups and any of the above groups substituted with one or more hydroxyl or zwitterionic groups Z, or R—X— is a nitrile group;

$R^3$ and $R^4$ are independently selected from the group consisting of linear and branched alkyl, alkenyl, and alkynyl groups, aryl, alkoxycarbonyl, alkylaminocarbonyl, cycloalkyl, cycloalkenyl, cycloalkynyl, haloaryl, haloalkyl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, alkylaminocarbonyl, oxacycloalkyl, oxacycloalkenyl, organosilane and organosiloxane groups and any of the above groups substituted with a zwitterionic group Z, an isocyanate group, a hydroxyl group or a polymerisable ethylenically unsaturated group;

$R^1$ and $R^2$ are independently selected from hydrogen and $C_1$–$C_{12}$ alkyl groups; and a first group selected from R, $R^3$, and $R^4$ contains an organosiloxane group Y and/or an organosilane group U, a second group selected from R, $R^3$ and $R^4$ is a hydrophilic group, and the third group selected from R, $R^3$ and $R^4$ comprises a polymerisable ethylenically unsaturated group or an isocyanate group.

In the definition of R, $R^3$ and $R^4$, any alkyl group or moiety is preferably $C_{1-18}$ alkyl, any alkenyl group or moiety is preferably $C_{2-18}$ alkenyl, any alkynyl group or moiety is preferably $C_{2-12}$ alkynyl, any aryl group or moiety is preferably $C_{6-24}$ aryl, any alkaryl group or moiety is preferably $C_{7-24}$ alkaryl and any aralkyl group or moiety is preferably $C_{7-24}$ aralkyl, any cycloalkyl group or moiety is preferably $C_{4-24}$ cycloalkyl, any cycloalkenyl group or moiety is preferably $C_{5-24}$ cycloalkenyl, any cycloalkynyl group or moiety is preferably $C_{5-24}$ cycloalkynyl.

A zwitterionic group Z preferably has the general formula (II)

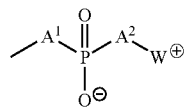
(II)

in which the moieties $A^1$ and $A^2$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group, preferably in which $W^+$ is a group of formula

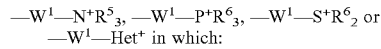

$W^1$ is alkanediyl of 1 or more, preferably 2–6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^5$ are the same or different and each is hydrogen or alkyl of 1 to 4 carbon atoms, preferably methyl, or aryl, such as phenyl, or two of the groups $R^5$ together with the nitrogen atom to which they are attached form an aliphatic heterocyclic ring containing from 5 to 7 atoms, or the three groups $R^5$ together with the nitrogen atom to which they are attached form a fused ring structure containing from 5 to 7 atoms in each ring, and optionally one or more of the groups $R^5$ is substituted by a hydrophilic functional group, and the groups $R^6$ are the same or different and each is $R^5$ or a group $OR^5$, where $R^5$ is as defined above; or Het is an aromatic nitrogen-, phosphorus- or sulphur-, preferably nitrogen-, containing ring, for example pyridine.

Most preferably the zwitterionic group of the formula (II), has the general formula (III):

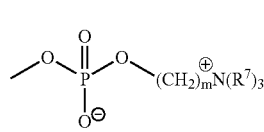
(III)

where the groups $R^7$ are the same or different and each is hydrogen or $C_{1-4}$ alkyl, and m is from 1 to 4, in which preferably the groups $R^7$ are the same preferably methyl.

Alternatively, the zwitterionic group may be a betaine group (ie. in which the cation is closer to the backbone), for instance a sulpho-, carboxy- or phospho-betaine. A betaine group should have no overall charge and is preferably therefore a carboxy- or sulpho-betaine. If it is a phosphobetaine the phosphate terminal group must be a diester, i.e., be esterified with an alcohol. Such groups may be represented by the general formula (IV)

(IV)

in which $A^3$ is a valence bond, —O—, —S— or —NH—, preferably —O—;

V is a carboxylate, sulphonate or phosphate diester (monovalently charged) anion;

$R^8$ is a valence bond (together with $A^3$) or alkanediyl, —C(O)alkylene- or —C(O)NHalkylene preferably alkanediyl, and preferably containing from 1 to 6 carbon atoms in the alkanediyl chain;

the groups $R^9$ are the same or different and each is hydrogen or alkyl of 1 to 4 carbon atoms or the groups $R^9$ together with the nitrogen to which they are attached form a heterocyclic ring of 5 to 7 atoms; and $R^{10}$ is alkyanediyl of 1 to 20, preferably 1 to 10, more preferably 1 to 6 carbon atoms.

One preferred sulphobetaine group has the formula (V)

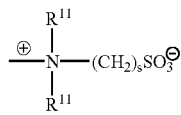

(V)

where the groups $R^{11}$ are the same or different and each is hydrogen or $C^{1-4}$ alkyl and s is from 2 to 4.

Preferably the groups $R^{11}$ are the same. It is also preferable that at least one of the groups $R^{11}$ is methyl, and more preferable that the groups $R^{11'}$ are both methyl.

Preferably s is 2 or 3, more preferably 3.

Alternatively the zwitterionic group may be an amino acid moiety in which the alpha carbon atom (to which an amine group and the carboxylic acid group are attached) is joined through a linker group to the backbone of the biocompatible polymer. Such groups may be represented by the general formula (VI)

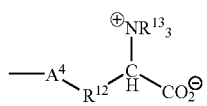

(VI)

in which $A^4$ is a valence bond, —O—, —S— or —NH—, preferably —O—, $R^{12}$ is a valence bond (optionally together with $A^4$) or alkanediyl, —C(O)alkylene- or —C(O)NHalkylene, preferably alkanediyl and preferably containing from 1 to 6 carbon atoms; and the groups $R^{13}$ are the same or different and each is hydrogen or alkyl of 1 to 4 carbon atoms, preferably methyl, or two or three of the groups $R^{13}$, together with the nitrogen to which they are attached, form a heterocyclic ring of from 5 to 7 atoms, or the three group $R^{13'}$ together with the nitrogen atom to which they are attached form a fused ring heterocyclic structure containing from 5 to 7 atoms in each ring.

$R^1$ and $R^2$ are preferably selected from hydrogen or $C_1$–$C_4$ alkyl groups, most preferably both hydrogen.

Most preferably the zwitterionic group is an ethylene-2-(trimethylammonium)ethylphosphate inner salt.

X is preferably a carbonyl group and adduct (I) has the formula

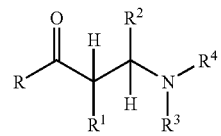

R preferably is a group selected from a group substituted by a zwitterionic group Z, hydroxyalkoxy, hydroxy and poly(oxyalkyl)oxy, most preferably hydroxyalkoxy.

When R comprises a zwitterionic group Z, R is preferably —OR', where R' is alkyl or aryl with substituents selected from groups (II), (III), (IV) and (VI).

Generally groups R, $R^3$, and $R^4$ have formula weights in the range 30–20,000.

When R contains a zwitterionic group, R preferably has a molecular weight in the range 150–400.

An organosiloxane group Y utilised in the present invention, for example as R, $R^3$ or $R^4$, preferably has the formula (VII)

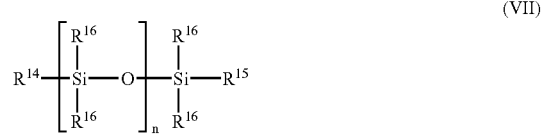

(VII)

in which $R^{14}$, $R^{15}$ and each $R^{16}$ are independently selected from monovalent groups selected from hydrogen, branched and straight $C_{1-12}$ alkyl, $C_{6-18}$ aryl, $C_{6-18}$ alkaryl, $C_{6-18}$ aralkyl, $C_{2-12}$ alkenyl, $C_{2-12}$ alkynyl and $(-OSiR^{16}_2)_pOSiR^{16}_3$, and divalent groups selected from a valence bond, branched and straight $C_{1-12}$-alkanediyl, $C_{6-18}$-arylene, $C_{7-18}$-alkarylene, $C_{12-2}$-alkenediyl and $C_{12-2}$-alkynediyl, any of which may be substituted by a primary, secondary or tertiary amine group and/or a group $XCH(R^1)CH(R^2)NR^3R^4$ or a group $-N(R^3)CH(R^2)CH(R^1)XR$ n is 0–300 and, p is 0 to 50, provided that at least one of the groups $R^{14}$, $R^{15}$ and $R^{16}$ is a divalent radical which is covalently bonded to the rest of the molecule I (VII) has a formula weight of 300–20000 Da, preferably 1000–7000, most preferably 3000–6000.

Where R is (VII), it is preferably connected to group X via the $R^{14}$ or $R^{15}$ group, preferably the $R^{14}$ group. Where this is the case, another of the groups $R^{14}$–$R^{16}$, preferably $R^{15}$, may be connected to another group $-XCH(R^1)CH(R^2)NR^3R^4$. Alternatively, or in addition to $R^{15}$ being connected to another such group, another of $R^{14}$ to $R^{16}$ may comprise an amine group, e.g. a $-NH_2$, $-NH(R^{17})$ or $-N(R^{17})_2$ group, wherein the or each $R^{17}$ is selected from linear and branched alkyl, alkenyl, and alkynyl groups, aryl, alkoxycarbonyl, alkylaminocarbonyl, cycloalkyl, cycloalkenyl, cycloalkynyl, haloaryl, haloalkyl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, alkylaminocarbonyl, oxacycloalkyl, oxacycloalkenyl, organosilane and organosiloxane groups and any of the above groups substituted with a zwitterionic group Z an isocyanate group, a hydroxyl group or a polymerisable ethylenically unsaturated group. Preferably $R^{17}$ is $C_{1-4}$-alkyl Preferably, each $R^{16}$ is selected from the group consisting of $C_{1-6}$ alkyl groups, preferably $C_{1-4}$ alkyl groups, most preferably methyl. Preferably the groups $R^{16}$ are the same.

Where $R^4$ comprises (VII), (VII) is preferably connected to the nitrogen atom of adduct (I) through group $R^{14}$ or $R^{15}$. Preferably the other of $R^{14}$ and $R^{15}$ is a group having a substituent $—N(R^3)CH(R^1)CH(R^2)XR$.

Preferably $R^{14}$ is selected from methanediyl, ethanediyl, propanediyl and butanediyl.

Preferably $R^{15}$ is either $C_{1-4}$-alkyl or $C_{1-4}$-alkyl substituted by a group $—N(R^3)CH(R^1)CH(R^2)XR$, preferably $R^3$, $R^1$, $R^2$, X and R having the same meanings as such groups in the core part of the molecule of the formula I.

An oligo(alkoxy)alkyl or a hydroxyalkyl oligo(oxyalkyl) group which is $R^3$ or $R^4$ may have the formula (VIII)

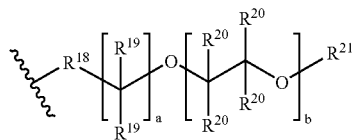

(VIII)

in which $R^{18}$ is a divalent group selected from a valence bond, $C_{61}$-alkanediyl, $C_{2-6}$-alkendiyl, $C_{6-18}$-arylene, $C_{7-18}$-alkarylene, and $C_{1-6}$-alkylamino $C_{1-6}$alkyl, any of which may be substituted by an amino group, each group $R^{19}$ and $R^{20}$ is independently selected from the group consisting of hydrogen, $C_{1-6}$ alkyl, $C_{6-18}$ aryl, $C_{6-18}$ aralkyl, $C_{6-18}$ alkaryl and $C_{2-6}$ alkenyl;

$R^{21}$ is selected from the group consisting of hydrogen, $C_{1-6}$ alkyl, $C_{6-18}$ aryl, $C_{6-18}$ aralkyl, $C_{2-6}$ alkenyl, aminoalkyl, mono-, di- and tri-alkylaminoalkyl, arylaminoalkyl, N-aryl-N-alkylaminoalkyl and -aminoaryl or any of the above groups substituted with a primary, secondary or tertiary amine group or a group $N(R^3)CH(R^2)CH(R^1)XR$;

a is an integer in the range of 0–10, provided that a $\geq 1$ when $R^{18}$ is a valence bond b is an integer in the range of 1–500, and (VIII) has a formula weight of 100–10000.

Each group $R^{19}$ is preferably selected from hydrogen or $C_{1-4}$ alkyl, more preferably hydrogen or methyl. Each group $R^{20}$ is preferably selected from hydrogen or $C_{1-4}$ alkyl, more preferably hydrogen or methyl, most preferably H. For instance one of the groups $R^{20}$ may be a methyl and the rest hydrogen, but most preferably all $R^{20}$ groups are hydrogen.

Preferably (VIII) has a formula weight in the range 300–10000, more preferably 400–7000, more preferably 500–6000, most preferably 500–2000.

An oligo(alkoxy)alkoxy group R has the formula

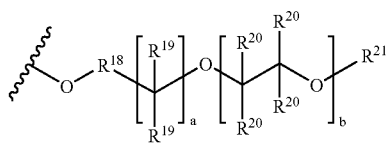

wherein the groups $R^{18}$ to $R^{21}$ a and b have the same meanings as in VIII.

Preferably $R^4$ is a polysiloxane represented by (VII), $R^3$ comprises an ethylenically unsaturated group, and R is a hydrophilic group, for instance a group comprising a zwitterionic group Z, more preferably a zwitterionic group (III), a $C_{1-12}$ hydroxyalkoxy group or a group of formula V(III).

Where one of R, $R^3$ and $R^4$ does not contain an organosiloxane group, at least one of R, $R^3$ and $R^4$ is an organosilane group U. A preferred organosilane group for use in the present invention has the general formula (IX)

wherein each $R^{23}$ is selected from the group consisting of hydrogen, branched and straight $C_{1-12}$ alkyl, $C_{6-18}$ aryl, $C_{6-18}$ alkaryl, $C_{6-18}$ aralkyl, $C_{2-12}$ alkenyl and $C_{2-12}$ alkynyl; and $R^{22}$ is selected from the group consisting of a valence bond, branched and straight chain $C_{1-12}$ alkanediyl, straight and branched $C_{2-12}$ alkenediyl and straight and branched $C_{2-12}$ alkynediyl.

Preferably each $R^{23}$ is $C_{1-4}$ alkyl, preferably the same alkyl group.

Preferably $R^{22}$ is a $C_{1-6}$ alkanediyl, more preferably $C_{1-4}$ alkanediyl, most preferably 1,3-propanediyl.

An organosilane group (IX) preferably has a formula weight in the range 100–350.

In a preferred embodiment in which the adduct is a prepolymer or macromer $R^3$ comprises an ethylenically unsaturated group or an isocyanate group that is capable of polymerising with comonomers. Such reactive groups may additionally allow derivatisation of the adduct by conjugation to drugs, ligands or biological molecules such as enzymes or heparin.

Where $R^3$ comprises an ethylenic group, such a group is preferably selected from the group consisting of (meth)acryloyloxy, (meth)acrylamido and allyl groups.

Where $R^3$ comprises an isocyanate substituent $R^3$ is preferably a cycloalkylaminocarbonyl, arylaminocarbonyl, or alkylaminocarbonyl group containing an isocyanate substituent.

In a further aspect of the invention there is provided a compound of the general formula

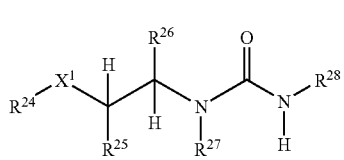

X in which $X^1$ is an electron withdrawing group selected from the group consisting of carbonyl and sulphone groups, sulphonium and phosphonium salts;

$R^{24}$ is selected from the group consisting of hydrogen, linear and branched alkyl, alkenyl, alkynyl, cycloalkyl, cycloalkenyl, cycloalkynyl, aryl, alkaryl, aralkyl, alkoxyaryl, alkoxyalkyl, oligoalkoxyalkyl, di-alkylaminoalkyl, N-aryl-N-alkylaminoalkyl, hydroxyalkoxy, alkoxy, alkenyloxy, alkynyloxy, cycloalkoxy, cycloalkenyloxy, cycloalkynyloxy, aralkoxy, alkoxyaryloxy, alkoxyalkoxy, oligoalkoxyalkoxy, di-alkylaminoalkoxy, N-aryl-N-alkylamino-alkoxy, acyloxy, acyloxyalkyl, N-diacyl-iminoalkyl groups, organosilane, organosiloxane, hydroxyaryl, hydroxyalkenyl, hydroxyalkynyl and hydroxy groups and any of the above groups substituted with one or more hydroxyl or zwitterionic groups Z or $-R^{24}\ X^1$ is a nitrile group;

$R^{25}$ and $R^{26}$ are independently selected from hydrogen and $C_1$–$C_{12}$ alkyl groups;

$R^{27}$ is an optionally substituted alkyl, alkenyl, alkynyl, aryl, cycloalkyl, cycloalkenyl or cycloalkynyl group; and $R^{28}$ is an optionally substituted alkyl, alkenyl, alkynyl, aryl, cycloalkyl, cycloalkenyl or cycloalkynyl group.

$X^1$ is preferably a carbonyl group.

$R^{24}$ is preferably a hydrophilic group, more preferably selected from a zwitterionic or hydroxyl substituted alkoxy, alkoxyalkoxy or oligoalkyoxyalkoxy group. A zwitterionic group is preferably a group Z as defined in relation to the first aspect of the invention.

$R^{25}$ and $R^{26}$ are preferably selected from hydrogen or $C_1$–$C_4$ alkyl groups, most preferably both are hydrogen.

Optional substituents in $R^{27}$ and $R^{28}$ are preferably selected from hydroxyl, alkoxy, acyl, acyloxy, acylamino, isocyanate, amine, zwitterions, aryl, alkenylaryl and alkenyloxy groups and may comprise polymeric moieties.

One group of compounds of the general formula X comprises polymerisable compounds, in which one of the groups $R^{24}$, $R^{27}$ and $R^{28}$ comprises a polymerisable group, preferably selected from an ethylenically unsaturated group, an isocyanate or an active hydrogen containing group, preferably part of a substituent on an alkyl group. Most preferably it is group $R^{28}$ which comprises such a polymerisable group. Active hydrogen groups may react with isocyanate groups to form urethane, ureido or thiourea linkages. $R^{28}$ is preferably alkenylphenyl, allyl, 2-(meth)acryloyloxyethyl, isocyanatoalkyl or isocyanatoalkylarylalkyl.

Preferably $R^{27}$ is selected among the preferred groups defined above for $R^4$.

Where a substituent comprises a polymeric moiety, this may be the homo- or co-polymerisation product of a compound of the general formula X. Thus a substituent may comprise the product of the polymerisation of an ethylenically unsaturated compound having the general formula X, or the product of the reaction of a compound of the general formula X having at least two isocyanate substituents with a coreactive compound having at least two active hydrogen atoms (e.g. a diamine or diol), or alternatively of a compound of the general formula X having at least two active hydrogens with a coreactive di- or higher-isocyanate compound.

In one preferred embodiment which is a macromer of both first and second aspects, an adduct has the formula (XI) or (XII);

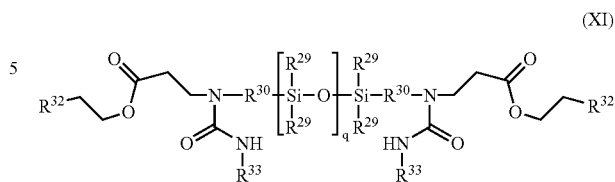

(XI)

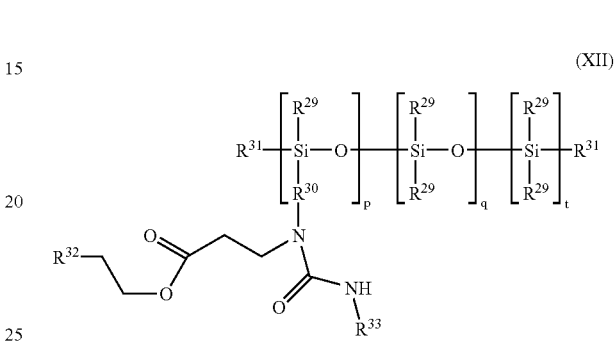

(XII)

wherein each group $R^{29}$ and each group $R^{31}$ is independently selected from the group consisting of hydrogen, $C_{1-6}$ alkyl, $C_{6-8}$ aryl, $C_{6-18}$ aralkyl, $C_{6-18}$ alkaryl, and $C_{2-6}$ alkenyl, preferably $C_{1-6}$ alkyl, most preferably methyl or ethyl;

the or each $R^{30}$ is independently selected from the group consisting of $C_{1-6}$ alkanediyl, $C_{2-6}$ alkendiyl and $C_{2-6}$ alkynediyl, preferably $C_{1-6}$ alkanediyl; the or each $R^{32}$ is selected from the group consisting of hydroxyl, hydroxyalkoxy, hydroxy(oligoalkoxy) and a zwitterionic group Z;

the or each $R^{33}$ is individually selected from the group consisting linear and branched alkyl, aryl, alkenyl, and alkynyl groups, cycloalkyl, cycloalkenyl, cycloalkynyl, aralkyl, alkaryl, alkoxyaryl, alkoxyalkyl, oligoalkoxyalkyl, arylaminoalkyl, N-aryl-N-alkylaminoalkyl, acyloxyalkyl (including alkenoyloxyalkyl), acylaminoalkyl, acylaminocycloalkyl, acylaminoaryl, N,N-diacyl-iminoalkyl groups, any of the above groups not comprising an ethylenically unsubstituted group being substituted with an isocyanate group;

p is an integer of 1 to 50;

q is an integer of 1 to 500;

r is an integer of 1 to 50; and t is 0 or 1.

In the formula (XI) and (XII) the order of the siloxyl groups is not intended to represent the specific order within the organosiloxane backbone and in fact these groups can be randomly or specifically ordered within the backbone.

Most preferably all of $R^{29}$ and any groups $R^{31}$ are methyl and $R^{30}$ is selected from ethanediyl, propanediyl and butanediyl.

In a further preferred embodiment, compound X has the formula (XIII) or (XIV)

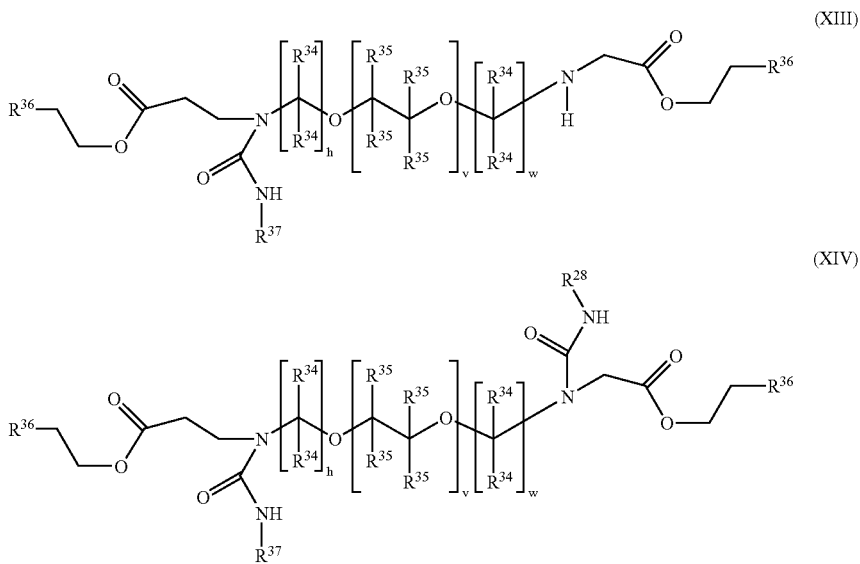

(XIII)

(XIV)

wherein each group $R^{34}$ and $R^{35}$ is independently selected from the group consisting of hydrogen, $C_{1-4}$ alkyl, $C_{6-18}$ aryl, $C_{6-18}$ aralkyl, $C_{6-18}$ alkaryl; and $R^{36}$ is selected from the group consisting of hydroxy, hydrogen, $C_{2-6}$ alkenoyloxy, organosilane and organosiloxane groups;

u is an integer of 1–10, v is an integer of 1–500, w is an integer of 1–10; and $R^{28}$ is an optionally substituted alkyl, alkenyl, alkynyl, aryl, cycloalkyl, cycloalkenyl or cycloalkynyl group.

Preferably each $R^{34}$ and $R^{35}$ is selected from propyl, ethyl, methyl and hydrogen and are preferably all the same, more preferably hydrogen. One of the groups $R^{35}$ may be methyl.

Preferably any substituent in $R^{28}$ is selected from hydroxyl, alkoxy, acyl, acyloxy, acylamino, isocyanate amine, zwitterions, aryl, alkenylaryl and alkenyloxy groups and may comprise polymeric moieties. More preferably $R^{28}$ includes a substituent which includes an ethylenically unsaturated group, for instance an alkenoyloxy substituent on an alkyl or on an aryl- or alkyl-aminocarbonyloxy, or aryl- or alkyl-aminocarbonylamino group. Alternatively $R^{28}$ includes an isocyanate substituent, preferably in an alkyl, alkaryl, aralkyl or aryl group.

According to a third aspect of the invention there is provided a hydrophilised organo siloxane prepolymer of the general formula XV

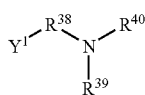

XV in which $Y^1$ is an organosiloxane group of the general formula VII defined above;

$R^{38}$ is a valence bond, or where the divalent group $R^{14}$ or $R^{15}$ in group VII which is joined to $R^{38}$ is a valence bond, is a divalent group selected from straight and branched $C_{1-12}$ alkanediyl, $C_{6-18}$ arylene, $C_{7-18}$-alkarylene, $C_{2-12}$-alkenediyl and $C_{2-12}$-alkynediyl;

$R^{39}$ is an organic group comprising an ethylenically unsaturated moiety; and $R^{40}$ is a hydrophilic organic group.

In this aspect of the invention a hydrophilic group is a group which confers increased hydrophilicity on the compound of the general formula XV than the corresponding compound in which $R^{40}$ was replaced by a hydrogen atom. Preferably the hydrophilic linear, branched or cyclic group is an alkyl group having one or more hydroxyl, zwitterionic $C_{1-2}$ alkoxy, (oligo)hydroxy $C_{1-6}$ alkyoxy, hydroxyl $C_{1-6}$ alkoxy oligo ($C_{2-3}$ alkoxy), or $C_{21}$- alkoxy oligo ($C_{2-3}$ alkoxy) substituents. $R^{40}$ is preferably a group of the formula VIII above, or is an alkyl or alkoxy alkyl group having a zwitterionic substituent of the general formula II, IV, V or VI defined above, most preferably of the general formula III defined above.

$R^{39}$ is an organic group which comprises an ethylenically unsaturated moiety which confers radical polymerisability on the compound XV. The group may include one or more linking moieties such as urea, urethane, thiourea, amide or ester groups in combination with spacers, such as $C_{1-12}$ alkanediyl, $C_{2-12}$-alkenediyl, $C_{2-12}$-alkynediyl, arylene and alkarylene via which the ethylenically unsaturated moiety if joined to the core nitrogen atom.

In one embodiment $R^{39}$ is a group $R^{41}$ NHCO— in which $R^{41}$ is an alkyl, alkenyl, alkynyl, aryl, aralkyl, alkaryl, cycloalkyl, cycloalkenyl or cycloalkynyl group substituted by a group XVI

CH($R^{42}$)=CH($R^{43}$)L- (XVI)

in which $R^{42}$ is hydrogen, $C_{1-4}$ alkyl, or —COOR$^{44}$ in which $R^{44}$ is hydrogen or $C_{1-4}$ alkyl, $R^{43}$ is hydrogen, $C_{1-4}$ alkyl, or —COOR$^{44}$ in which $R^{44}$ is hydrogen or $C_{1-4}$ alkyl, provided that $R^{42}$ and $R^{43}$ are not both —COOR$^{44}$, and L is a divalent linker.

L is preferably joined to the carbon to which $R^{43}$ is joined by a divalent moiety selected from methylene, a valence bond, —COO—, —CON($R^{45}$)—, in which $R^{45}$ is hydrogen or $C_{1-4}$ alkyl, and arylene, which in turn is preferably joined to an alkanediyl, arylene, alkylaminocarbonylamino or arylaminocarbonylamino group.

In another embodiment of this aspect of the invention $R^{39}$ is an alkyl group substituted by a group including the ethylenically unsaturated moiety, usually a group of the formula XVI as defined above. For instance $R^{39}$ may be a methyl group with the said substituent or a 2-hydroxy-ethane-1-yl with a 2-substituent of the general formula XVI above.

According to a further aspect of the invention there is provided a first process, suitable for forming a compound of the general formula I as well as other compounds, in which:

in a first step a primary amine compound $R^{38}$ $NH_2$, in which $R^{38}$ is selected from linear and branched alkyl, alkenyl, and alkynyl groups, aryl, alkoxycarbonyl, alkylaminocarbonyl, cycloalkyl, cycloalkenyl, cycloalkynyl, haloaryl, haloalkyl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, alkylaminocarbonyl, oxacycloalkyl, oxacycloalkenyl, organosilane and organosiloxane groups and any of the above groups substituted with a zwitterionic group Z an isocyanate group, a hydroxyl group or a polymerisable ethylenically unsaturated group is reacted with Michael reagent of the formula $CH(R^{39})=CH(R^{40})X^2R^{41}$ in which $R^{39}$ and $R^{40}$ are independently selected from hydrogen and $C_{1-12}$ alkyl groups, $X^2$ is an electron withdrawing group selected from the group consisting of carbonyl and sulphone groups, sulphonium and phosphonium salts; and $R^{41}$ is selected from linear and branched alkyl, alkenyl, and alkynyl groups, aryl, alkoxycarbonyl, alkylaminocarbonyl, cycloalkyl, cycloalkenyl, cycloalkynyl, haloaryl, haloalkyl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, alkylaminocarbonyl, oxacycloalkyl, oxacycloalkenyl, organosilane and organosiloxane groups and any of the above groups substituted with a zwitterionic group Z an isocyanate group, a hydroxyl group or a polymerisable ethylenically unsaturated group to form a secondary amine intermediate $R^{38}$ $NHCH(R^{39})CH(R^{40})X^2R^{41}$, and in a second step the secondary amine intermediate is reacted with an isocyanate compound $R^{42}$ NCO which reacts at the nitrogen atom of the secondary amine group to form a ureido bond, in which $R^{42}$ is an alkyl, aryl, alkaryl or aralkyl group optionally substituted by isocyanate or acyloxy groups;

in which one of $R^{38}$ and $R^{41}$ contains an organosiloxane group $Y^1$ or an organosilane group U, one of $R^{38}$, $R^{41}$ and $R^{42}$ comprises an ethylenically unsaturated group or is a hydrophilic group.

The product of the two step reaction is believed to have the formula XVII

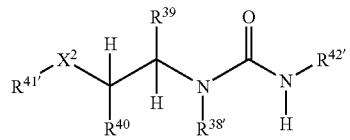

where $R^{41'}$ and $R^{38'}$ are the same as $R^{41}$ and $R^{38}$ respectively, or if $R^{38}$ contains one or more NH substituents or, if $R^{41}$ contains one or more —$X^2CH(R^{40})=CH(R^{39})$ substituents, may be the corresponding derivatised groups from the first reaction step, and, if $R^{42}$ comprises 1 or more isocyanate groups $R^{42'}$ may be the residue of the oligomerisation of two di- or higher-functional intermediate and isocyanate compounds, otherwise $R^{42'}$ is the same as $R^{42}$.

The definitions of the variable groups in the formula XVII may be such that the compound XVII is a compound of the general formula I as defined above. In some instances one or more of the groups $R^{38'}$, $R^{41'}$ or $R^{42'}$ may require further derivatisation to form the novel compound of the first aspect. For instance where none of the groups $R^{38'}$, $R^{41'}$ or $R^{42'}$ comprises an ethylenically unsaturated group, such a group may be introduced in a further step in which the respective group having an appropriate functional substituent is reacted with a further coreactive ethylenically unsaturated reagent optionally with a linker compound to introduce an ethylenic group. Thus $R^{38'}$, $R^{41'}$ or $R^{42'}$ may comprise an isocyanate group which may be reacted in a further step with an ethylenically unsaturated compound having an active hydrogen whereby a ureido, urethane or thiourea linkage is formed and the product includes an ethylenically unsaturated group. Other bonds may be generated instead of the urea, this urea or urethane bond, such as amide or ester using conventional reactive compounds.

Similarly where none of $R^{38'}$, $R^{41'}$ or $R^{42'}$ is a hydrophilic group, such a group may be introduced in a third step in which the respective group is derivatised with a hydrophilising reactant. Thus an isocyanate group on $R^{38'}$, $R^{41'}$ or $R^{42'}$ as the case may be, may be reacted with a hydrophilic compound having an active hydrogen, such as aminofunctional polyethyleneglycol. Again bonds other than urea, urethane or thiourea e.g. amide or ester may be generated instead by use of appropriate reagents.

The further reaction to introduce a hydrophilic group, if it involved a di- or higher-functional hydrophilising reagent, and where an organosiloxane group $Y^1$ which is in $R^{38}$ or $R^{41}$ includes one or more amine groups, or one or more substituents —$X^2CH(R^{40})=CH(R^{39})$, as the case may be, may be a polymerisation reaction.

Preferably the product of the reaction is not chainlengthened to such an extent that the molecular weight is increased to a level at which it is difficult to solubilise to form a homogeneous solution.

Where the product of the two step reaction is other than a copound within the general formula I it may be a useful intermediate for forming other end products. For instance, $R^{38'}$, $R^{41'}$ or $R^{42'}$ may be derivatised to conjugate ligands or surface-binding groups, including hydrophobic, ionic or reactive groups.

A further aspect of the present invention provides a method wherein an organosiloxane bearing at least one primary amine group may be sequentially functionalised, initially by an alkylation step and subsequently by a second step to introduce different functionalities to the molecule.

Such functionalities may introduce chemical reactivity, and/or physical properties such as hydrophobicity/hydrophilicity to the molecule. In particular, the invention provides a method in which an amino-functional organosiloxane compound of the formula (XXI)

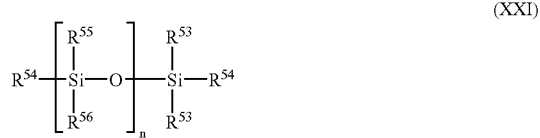

(XXI)

in which $R^{53}$–$R^{56}$ are each selected from $C_{1-12}$ alkyl, $C_{2-12}$ alkenyl and $C_{2-12}$ alkynyl, $C_{6-18}$ aryl, $C_{7-18}$ aralkyl and $C_{7-18}$ alkaryl, any of which may be substituted by a primary amine group, and n is 0–300, provided that at least 1 of the groups $R^{53}$ to $R^{56}$ is substituted by a primary amine group, is reacted in a first reaction with a first reagent to form a secondary amine product (XXV) in which one of the active hydrogens of the said at least one primary amine group is replace, by a group $R^{57}$ which is joined to the nitrogen atom through a

link wherein the groups $R^{58}$ are each hydrogen, $C_{1-12}$ alkyl or $C_{1-12}$ alkenyl;

$R^{57}$ is selected from the group consisting of linear and branched alkyl, alkenyl, alkynyl, cycloalkyl, cycloalkenyl, cycloalkynyl, haloaryl, haloalkyl, aryl, aralkyl, alkaryl, alkoxyaryl, alkoxyalkyl, oligoalkoxyalkyl, aminoalkyl, mono-, di- and tri-alkylaminoalkyl, arylaminoalkyl, N-aryl-N-alkylaminoalkyl aminoaryl, alkoxyalkyl, alkenyloxyalkyl, alkynyloxyalkyl, cycloalkoxyalkyl, cycloalkenyloxyalkyl, cycloalkynyloxyalkyl, haloalkoxyalkyl, aralkoxyalkyl, alkoxyaryloxyalkyl, oligoalkoxyalkyl, aminoalkoxyalkyl, mono-, di- and tri-alkylaminoalkoxyalkyl, arylaminoalkoxyalkyl, N-aryl-N-alkylamino-alkoxyalkyl, acyloxyalkyl, acylaminoalkyl, N-diacyl-iminoalkyl groups, alkylamino, oxacycloalkyl, oxacycloalkenyl, organosilane, organosiloxane, hydroxyalkyl, and hydroxyalkenyl groups and any of the above groups substituted with one or more zwitterionic group Z; and the secondary amine is reacted in a second reaction with at least one second isocyanate reagent whereby the remaining active hydrogen attached to the secondary amine group is replaced by an organic radical joined through a ureido link.

In the definition of $R^{57}$ any alkyl group or moiety is preferably $C_{1-18}$ alkyl, any alkenyl group or moiety is preferably $C_{2-18}$ alkenyl, any alkynyl group or moiety is preferably $C_{2-12}$ alkynyl, any aryl group or moiety is preferably $C_{6-24}$ aryl, any alkaryl group or moiety is preferably $C_{7-24}$ alkaryl and any aralkyl group or moiety is preferably $C_{7-24}$ aralkyl, any cycloalkyl group or moiety is preferably $C_{4-24}$ cycloalkyl, any cycloalkenyl group or moiety is preferably $C_{5-24}$ cycloalkenyl, any cycloalkynyl group or moiety is preferably $C_{5-24}$ cycloalkynyl.

Preferably $R^{53}$–$R^{56}$ are each selected from $C_{1-8}$ alkyl, $C_{2-8}$ alkenyl and $C_{2-8}$ alkynyl, $C_{6-12}$ aryl, $C_{7-12}$ aralkyl and $C_{7-12}$ alkaryl, any of which may be optionally substituted by a primary amine group. Of those groups $R^{53}$–$R^{56}$, not substituted by an amine, they are preferably $C_{1-4}$ alkyl or $C_{2-4}$ alkenyl, most preferably methyl, ethyl, propyl, and mixtures thereof. Those of $R^{53}$–$R^{56}$ substituted by an amine are preferably selected from the group consisting of aminomethyl, aminoethyl, aminopropyl, aminobutyl and mixtures thereof.

Preferably $R^{54}$ comprise the primary amine groups. More preferably $R^{54}$ and amino-$C_{1-6}$-alkyl groups, most preferably amino methyl, aminoethyl, aminopropyl, or aminobutyl.

In a preferred embodiment the organosiloxane (XXI) has molecular weight in the range of 300–20000 and comprises at least one primary amine group, more preferably 1–20 primary amine groups, more preferably 2–10 primary amine groups, most preferably 2 primary amine groups.

In one preferred embodiment, the first reagent is a compound $R^{60}$—X where X is a halogen atom and $R_{60}$=$R^{57}C(R^{58})_2$ and is an optionally substituted $C_{1-18}$ alkyl, $C_{2-18}$ alkenyl or $C_{6-24}$ aryl group, optional substituents being selected from halogen, $C_{3-12}$ alkanoyloxy, $C_{4-12}$ alkanoyloxy-$C_{1-12}$-alkyl, $C_{3-12}$ alkanoylamino, $C_{4-12}$ alkenoyloxy, $C_{4-12}$ alkenoylamino, carboxylic acid, $C_{2-12}$ alkenyl, methacryloyloxy and acryloyloxy.

Most preferably the first reagent, $R^{60}$—X, is chloromethylstyrene.

In another preferred embodiment, the first reagent has the formula

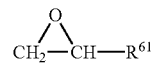

where $R^{61}$ is selected from the group consisting of hydrogen, $C_{1-12}$ alkyl, $C_{3-12}$ alkanoyloxy-$C_{1-12}$-alkyl, $C_{4-12}$ alkenoyloxy-$C_{1-12}$-alkyl and $C_{2-12}$ alkenyl.

Most preferably the first reagent

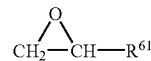

is glycidoxymethacrylate.

The first alkylation step may be performed by any type of alkylation reaction including Michael addition according to the first aspect of the invention.

In a preferred embodiment, the second reagent is an isocyanate bearing compound (XXII), whereby the second reaction creates a ureido linkage with the product of (XXI) and the first reagent.

Compound (XIX) may undergo a second reaction with an isocyanate bearing compound (XXII), whereby the second reaction creates a ureido linkage.

Preferably the isocyanate (XXII) has the formula $R^{51}(NCO)_m$, where $R^{51}$ is an m-functional organic radical where m is an integer of 1–10. More preferably m is an integer of 1 or 2.

Preferably $R^{51}$ is selected from the group consisting of linear and branched alkyl, alkenyl, and alkynyl groups, cycloalkyl, cycloalkenyl, cycloalkynyl, haloaryl, haloalkyl, aryl, aralkyl, alkaryl, alkoxyaryl, alkoxyalkyl, oligoalkoxyalkyl, acyloxy (including alkenoyloxyalkyl), acyloxyalkyl (including alkenoyloxyalkyl), acylaminoalkyl, N-diacyliminoalkyl groups, alkylaminocarbonyl, oxacycloalkyl, oxacycloalkenyl, organosilane bonded to the $(NCO)_m$ through an alkyl group, and organosiloxane groups and any of the above groups substituted with a zwitterionic group Z, or an organosiloxane group.

In the definition of $R^{51}$, any alkyl group or moiety is preferably $C_{1-18}$ alkyl, any alkenyl group or moiety is preferably $C_{2-18}$ alkenyl, any alkynyl group or moiety is preferably $C_{2-12}$ alkynyl, any aryl group or moiety is preferably $C_{6-24}$ aryl, any alkaryl group or moiety is preferably $C_{7-24}$ alkaryl and any aralkyl group or moiety is preferably $C_{7-24}$ aralkyl, any cycloalkyl group or moiety is preferably $C_{4-24}$ cycloalkyl, any cycloalkenyl group or moiety is preferably $C_{5-24}$ cycloalkenyl, any cycloalkynyl group or moiety is preferably $C_{5-24}$ cycloalkynyl.

The reaction of (XXII) with compound (XIX) forms a compound having the formula (XXIII)

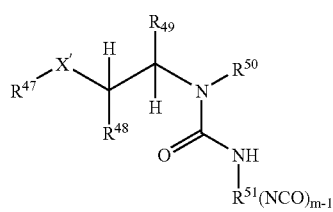

(XXIII)

wherein m=1–10, preferably 1–5 most preferably 2.

In one particularly preferred embodiment, $R^{51}$ comprises a site of unsaturation, most preferably an isocyanate group capable of crosslinking to another compound of general structure (XIX), another compound, polymer or group, or alternatively a substrate as defined hereinbefore. Said site of unsaturation may alternatively provide a site at which homo or co-polymerisation of a compound (XXII) may occur, for example an ethylenically unsaturated group such as (meth) acryloyloxy.

Most preferably the compound (XXII) is an isocyanate or diisocyanate selected from the group consisting of $C_{2-30}$ aliphatic, $C_{6-30}$ aromatic and $C_{6-20}$ alicyclic diisocyanates $C_{4-30}$ allyl isocyanates, $C_{3-30}$ isocyanatoalkylacrylates, $C_{5-30}$ isocyanato alkylmethacrylates, more preferably preferably allyl isocyanate, dimethyl meta-isopropenylbenzylisocyanate, isophorone diisocyanate, hexamethylene diisocyanate, meta-tetramethylxylylene diisocyanate.

Where (XXII) is a diisocyanate compound, the reaction with (XIX) may leave the second isocyanate moiety unreacted. This can then be used to crosslink or chain-extend the compound (XIX). Crosslinking may occur with another adduct (XIX) or compound bearing an active >NH or —NH$_2$ group. Reaction of the second isocyanate may take place with a compound bearing is a hydroxy group to form a urethane linkage.

In an alternative reaction to that between (XIX) and (XXII), the compound (XIX) may undergo a second reaction with a compound (XXIV)

$$R^{52}\text{-Q} \quad (XXIV)$$

wherein Q is a halogen atom, preferably chlorine or bromine; and $R^{52}$ is selected from the group consisting linear and branched alkyl, alkenyl, and alkynyl groups, alkoxycarbonyl, alkylaminocarbonyl, cycloalkyl, cycloalkenyl, cycloalkynyl, haloaryl, haloalkyl, aryl, aralkyl, alkaryl alkoxyaryl, alkoxyalkyl, oligoalkoxyalkyl, aminoalkyl, mono-, di- and tri-alkylaminoalkyl, arylaminoalkyl, N-aryl-N-alkylaminoalkyl and -aminoaryl, acyloxyalkyl, alkenoyloxy, alkenoyloxyalkyl, acylaminoalkyl, N-diacyl-iminoalkyl groups, alkylaminocarbonyl, oxacycloalkyl, oxacycloalkenyl, organosilane and organosiloxane groups and any of the above groups substituted with a zwitterionic group Z.

In the definition of $R^{52}$, any alkyl group or moiety is preferably $C_{1-18}$ alkyl, any alkenyl group or moiety is preferably $C_{2-18}$ alkenyl, any alkynyl group or moiety is preferably $C_{2-12}$ alkynyl, any aryl group or moiety is preferably $C_{6-24}$ aryl, any alkaryl group or moiety is preferably $C_{7-24}$ alkaryl and any aralkyl group or moiety is preferably $C_{7-24}$ aralkyl, any cycloalkyl group or moiety is preferably $C_{4-24}$ cycloalkyl, any cycloalkenyl group or moiety is preferably $C_{5-24}$ cycloalkenyl, any cycloalkynyl group or moiety is preferably $C_{5-24}$ cycloalkynyl.

Preferably $R^{52}$ comprises a site of unsaturation, preferably an ethylenically unsaturated group.

Most preferably $R^{52}$ is selected from the group consisting of $C_{1-8}$ alkyl, $C_{2-10}$ alkenyl, and $C_{2-10}$ alkynyl groups, particularly styrylmethylene.

Most preferably Q is a chlorine atom.

The reaction of (XXIV) with (XIX) generally results in the elimination of HQ, preferably HCl.

In a further aspect of the present invention there is provided an organosiloxane product having formula (XXV)

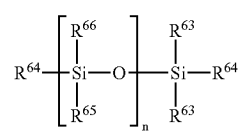

(XXV)

in which n is 0–300; and at least one of $R^{63}$–$R^{66}$ is a group

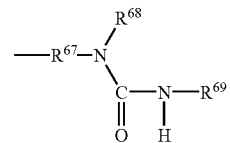

where $R^{67}$ is selected from the group consisting of $C_{1-12}$ alkanediyl, $C_{1-24}$ alkanediyloxyalkanediyl, (oligoalkanediyloxy)alkanediyl, $C_{1-24}$ alkanediylcarbonylaminoalkanediyl and $C_{1-18}$ alkanoyloxyalkanediyl;

$R^{68}$ is a hydrophilic group; and $R^{69}$ is selected from the same group as $R^{51}$ as defined above.

Preferably at least 1 of the groups $R^{64}$ is the group $R^{67}$.

For those groups $R^{63}$–$R^{66}$ which are not $R^{67}$, they are selected from $C_{1-12}$ alkyl, $C_{1-12}$ alkenyl, $C_{1-12}$alkynyl, preferably, $C_{1-6}$ alkyl, most preferably methyl and are preferably all the same.

Any of groups $R^{63}$–$R^{66}$ may be substituted with an amine group, preferably a primary or secondary amine group.

Preferably, $R^{67}$ is a $C_{1-4}$ alkanediyl group, most preferably methanediyl, ethanediyl, propanediyl or butanediyl.

$R^{68}$ is preferably a hydroxyalkoxyacyl or alkoxyacyl group optionally substituted with a zwitterionic group or a hydroxy group, most preferably $R^{68}$ is $HOCH_2CH_2OC(O)CH_2CH_2—$.

In a particularly preferred embodiment, $R^{69}$ is a group $R^{70}(NCO)_m$ wherein m is 0–10, preferably 1–5 most preferably 1 and $R^{70}$ is selected from the group consisting linear and branched alkyl, alkenyl, and alkynyl groups, cycloalkyl, cycloalkenyl, cycloalkynyl, haloaryl, haloalkyl, aryl, aralkyl, alkaryl, alkoxyaryl, alkoxyalkyl, oligoalkoxyalkyl, arylaminoalkyl, N-aryl-N-alkylaminoalkyl and -aminoarylalkyl, acyloxy (including alkenoyloxyalkyl), acyloxyalkyl (including alkenoyloxyalkyl), acylaminoalkyl, N-diacyliminoalkyl groups, alkylaminocarbonyl, oxacycloalkyl, oxacycloalkenyl, organosilane bonded to the $(NCO)_m$ through an alkyl group, and organosiloxane groups and any of the above groups substituted with a zwitterionic group Z.

The overall reaction for the first aspect of the present invention may be carried out in a single or multiple steps, preferably a single or two steps.

If Michael addition is to be followed by a functionalisation of the resultant secondary amine a two step reaction may be desirable as this allows work up of a characterisable, pure product after the first step. The reaction, however does not necessarily require an intermediate work-up and a 'one pot' reaction is preferable.

The first and third process aspects of the present invention must be carried out in at least two steps, the first being the alkylation reaction and the second being the subsequent functionalisation of the secondary amine product. Again, a 'one pot' reaction is preferable without intermediate work up.

The first step (reaction of the α, β-unsaturated group with amine-bearing component or the alkylation of (XXV)) may be performed in a solventless system when one component is able to solubilise the other. Alternatively, an aqueous or organic solvent may be utilised. Preferred organic solvents include alcohols (including hydroxyalkyl(meht)acrylate, particularly hydroxyethyl methacrylate), chlorinated hydrocarbons, organosulphoxides, amides and ethers.

Where (I) or (XXV) contains an ester linkage, one prerequisite for the Michael addition step is that the solvent in which the reaction occurs is chosen carefully in order to avoid the possibility of transesterification of the ester linkage in the resulting adduct. Transesterifications are acid or base catalysed reactions and it is likely that the basic structure of the secondary amine in the adduct is sufficient to catalyse the convertion. In particular it is found that the use of methanol as a reaction solvent results in a Michael adduct that has been almost exclusively transesterified, producing the methyl ester of the amine. When isopropylalcohol is used instead of methanol, the transesterification is virtually eliminated with only traces of the transesterified product being detected. Acidity, nucleophilicity and steric hinderance of the alcohol group are all considerations in determining whether the solvent system used will be suitable for the Michael addition.

The second step of the reaction (reaction of (XXII) with (XIX) or reaction of (XXII) with (XXV)) may be carried out in a solventless system or in aqueous or organic solvents. As the reaction proceeds an organic solvent is usually required. Preferred organic solvents include alcohols, chlorinated hydrocarbons, organosulphoxides, amines and ethers.

Where the second step of the reaction is carried out using a compound (XXIV), the reaction may be carried out in a solventless system or in aqueous or organic solvents. Preferred solvents include amides, for example dimethylacrylamide, and alcohols, for example, isopropylalcohol or hydroxyethyl methacrylate.

A particularly preferred solvent for the first reaction is isopropanol. For the second reaction, the preferred solvents include dimethylsulphoxide, isopropanol, hydroxyethyl methacrylate, tetrahydrofuran, ethanol, or N-methylpyrrolidone.

With regard to the first aspect of the invention, Scheme 1 shows two reaction routes resulting in particularly preferred products.

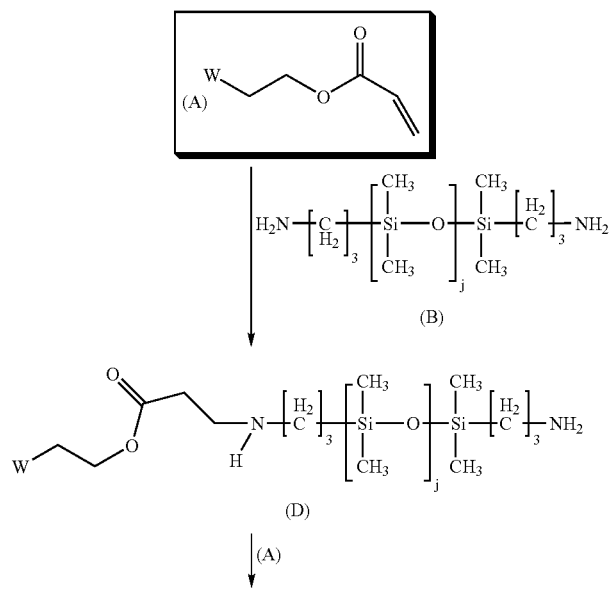

Scheme 1

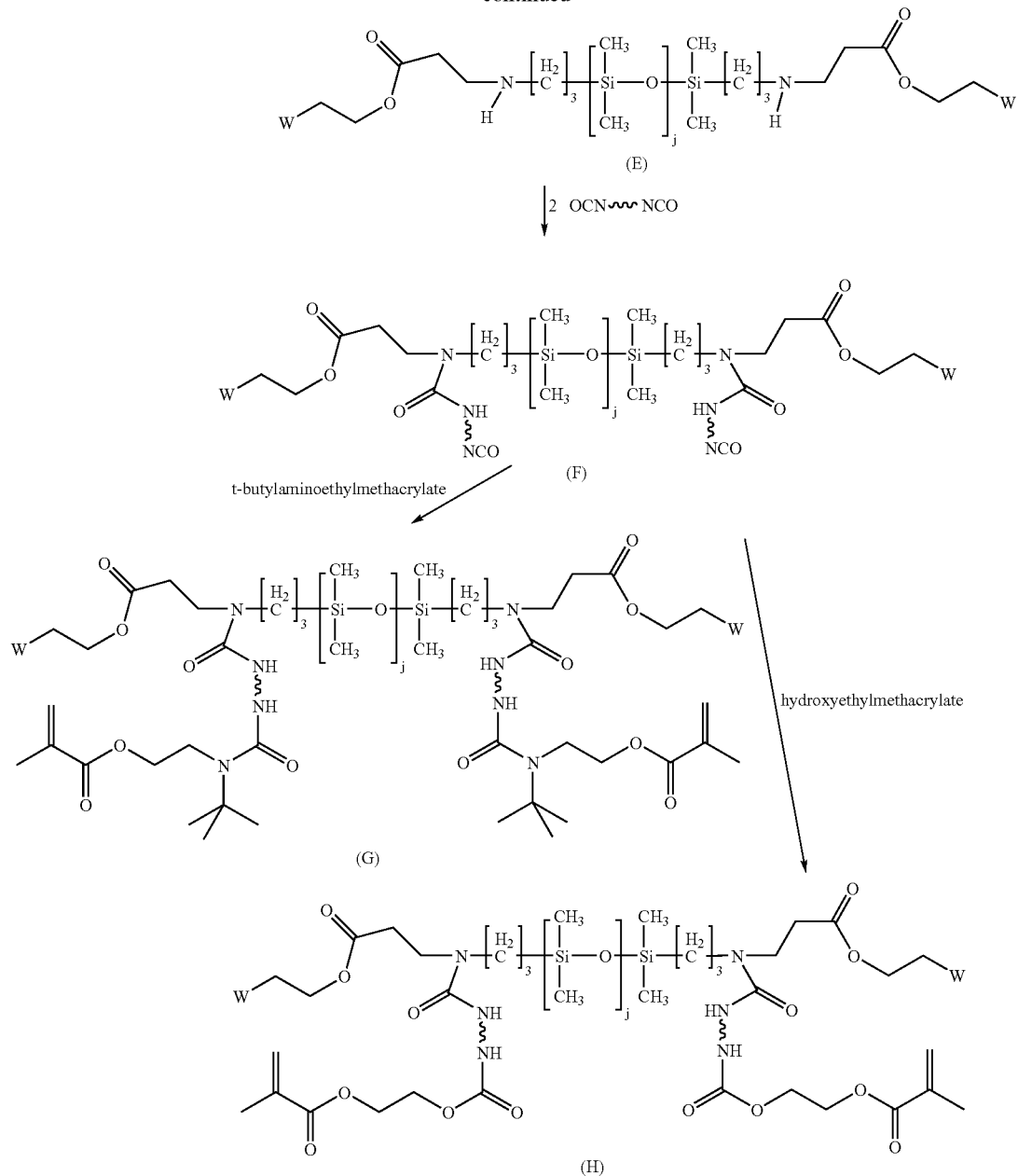

(E)

(F)

(G)

(H)

wherein j is an integer of 10–400. In scheme 1 W represents a phosphorylcholine group. It could be replaced by another hydrophilic substituent.

In scheme 1, the first two steps may be carried out separately or concurrently depending on the stoichiometry of the reaction. Preferably the production of (E) by the group (A) and (B) occurs in one step. The reaction product may be recovered and the further step of reaction with a reactive group (in the examples shown, a diisocyanate), is carried out.

It should be understood that an organosiloxane, bearing pendant amine groups such as those in compound (XIV) may be used in the above scheme in replacement of compound (B)

For example, if a diisocyanate compound is used to functionalise compound (E) this will produce an isocyanate-functionalised oligomer that could form a block in a segmented polyurethane urea.

As shown in the lower part of scheme 1, reaction of a compound of type (F) with a capping compound, for example hydroxyethylmethacrylate or t-butylaminoethylmethacrylate, may be used to produce a methacrylate-terminated oligomer ideal for free-radical polymerisation with other ethylenically unsaturated monomers. This could also be achieved in one step if a Michael adduct of the type (XIX) is reacted with an isocyanate bearing unsaturation in some form. Particularly useful are isocyanates such as dimethylmeta-isopropenylbenzylisocyanate, allylisocyanate or methacryloloxyethylisocyanate.

A blend of primary or secondary amine bearing compounds may be added to the α, β-unsaturated group of, for example, compound (A) in order to produce a mixture of macromers. When these are reacted further with an isocyanate bearing unsaturation of some form, for example a pendant isocyanate group, the resultant mixture can be oligomerised or polymerised to produce macromers or polymers comprising a mixture of units having tailored physical properties.

Prior to introduction of a cap, compound (F), for example, could be reacted with a similar or dissimilar group (E), for example. Another amine (either having undergone or not undergone a Michael addition reaction) may be introduced to react with (F) as another way of adding additional entities with desired physical and/or chemical properties into the molecule.

The "other amine" is typically any diamine for which the ratio of diisocyanate is adjusted such that some chain extension of compound (F) occurs, prior to capping the molecule. The addition of the "other" amine is prior to cap addition and may be accompanied by further diisocyanate addition to maintain stoichiometry.

As discussed above, the Michael addition reaction may be carried out with either acrylate or methacrylate, although the former is more reactive. This factor may be exploited to generat a methacrylate-functional product by producing a mixed acrylate/methacrylate precursor as in example 13a. Michael addition with an amine-containing group can lead to selective addition to the acrylate functionality. The unreacted methacrylate group can undergo Michael addition with an alternative group, for example an amine containing compound with differing physical properties to the first amine-containing group, or be used as a polymerisable group.

Materials comprising the adducts and products described hereinbefore are of particular utility in medical device manufacture.

The organosiloxane containing adducts of either aspect the present invention, or polymers or copolymers produced by their polymerisation have particular utility in the manufacture of contact and intra ocular lenses. They provide high oxygen permeability and biocompatibility within the ocular environment.

The presence of a zwitterionic component in a polymer provided by polymerisation of an adduct or product of either aspect the present invention improves the biocompatibibility of the material compared with non-zwitterionic containing analogues. If, for example, it is desirable to make biodegradable materials, this could be achieved by the incorporation of a suitably labile chain extender, the degradation product being less toxic to the body than a similar compound not bearing a zwitterionic group. Similarly, wear-debris from a non-degradable implant or contact lens of the materials should also be of less risk than a similar material not bearing a zwitterionic group to the body or ocular environment.

The production of a polymer by homo- or co-polymerising an adduct or product of the present invention may be achieved by any known polymerisation method. As described above, an adduct having a site of unsaturation is capable of, for example, free radical polymerisation.

The present invention additionally incorporates compositions comprising adduct(s) and/or products of the present invention, and compositions of polymers produced by polymerisation of such an adduct.

It is particularly preferred to copolymerise adducts having ethylenically unsaturated groups with ethylenically unsaturated comonomers. The comonomers preferably include at least one hydrophobic monomer, at least one hydrophilic monomer and at least one cross-linker.

Hydrophilic comonomers are preferably selected from N-vinyl lactams, N,N-dimethyl(meth)acrylamide, (meth)acrylamide, hydroxy-$C_{1-4}$-alkyl(meth)acrylates, vinyl acetate, hydroxy-$C_{1-4}$alkyl(meth)acrylamides and glycerol (meth)acrylate, and mixtures thereof.

Hydrophobic comonomers preferably incude at least one organosilyl-group containing monomer, or a fluorinated monomer, or both, and optionlaly also at least one alkyl or aryl group containing monomer. The organosilyl monomer may be for instance (meth)acrylates of siloxy group substituted alkanols, such as tris(trialkylsiloxy)silylalkyl(meth)acrylates, pentaalkyl- and triaryldialkyl-disiloxanylalkyl (meth)acrylates, alkyldi(trialkylsiloxy)silylalkyl(meth)acrylates, heptaalkyl-cyclotetrasiloxysilylalkyl(meth)acryaltes, more preferably tris(trimethylsiloxy)silylpropyl methacrylate. A fluorinated monomer may be selected from vinyl monomers containing at least 3 fluorine atoms, for instance fluoralkyl-(meth)acryalates and -(meth)acrylamides. Specific examples are hexafluoroisopropyl(meth)acrylates and 1,1,2,2-tetrahydroperfluoro-$C_{4-12}$-alkyl-(meth)arylates and -(meth)acrylamides.

Other useful hydrophobic monomers include $C_{1-24}$-alkyl (meth)acrylates, mono- or di-$C_{3-24}$-alkyl(meth)acrylamides, styrene and its derivatives, mono- nad di-$C_{4-24}$-alkyl esters of maleic and itaconic acids, $C_{1-10}$-alkyl vnyl ethers, and vinyl esters of $C_{4-24}$-alkanoic acids.

Cross-linking agents have tow or more ethylenic groups. They may be water-soluble or water-insoluble. It may be desirable to include one or more water-soluble cross-linking agent, and one or more water-insoluble cross-linking agent. Suitable water-soluble agents are methylene bisacrylamide, ethyleneglycol dimethacrylate and diethylene glycol dimethacrylate. Suitable water-insoluble agents include di(meth)acrylic esters of aromatic diols such as bisphenol A dimathacrylate.

In a copolymerisation, the adduct of the invention is preferably included in the pmonomer mixture in an weight proportion in the range 10 to 95%, preferably 25 to 75%. The hydrophilic monomer is present in an amount in the range 2.5 to 90%, preferably 10 to 25%. The hydrophobic monomer is present in a preferred amount in the range 2.5 to 90%, more preferably 5 to 25%. The cross-linking agent is preferably present in an amount in the range 0.01 to 10%, more preferably 0.1 to 1.0%. Hydrophilic monomer contributes to higher water contents of the final polymer, whilst hydrophobic monomer of the fluorinated or silyl type contibutes to incresed oxygen permeability which may be of particular where the product is a lens. The level of cross-linking agent affects the water content and physical strength of the polymer. The presence of other hydrohobic monomer contributes also to physical strength.

Scheme 2 shows two particularly preferred embodiments of the second aspect of the invention. The first utilises a glycidoxymethacrylate first reagent with an amino-terminated organosiloxane (B). The oxiran functionality preferentially reacts with the amine groups, leaving the resultant molecule (i) with pendant methacrylate functionalities. Subsequent reaction is shown with an isocyanate group to produce compound (J)

In the second particularly preferred embodiment, the first reagent is chloromethylstyrene. This reacts the terminal amino groups of (B) and eliminates HCl to produce a styryl-functionalised organosiloxane (K). Again, a subsequent reaction with an isocyanate group yeilds a compound (L).
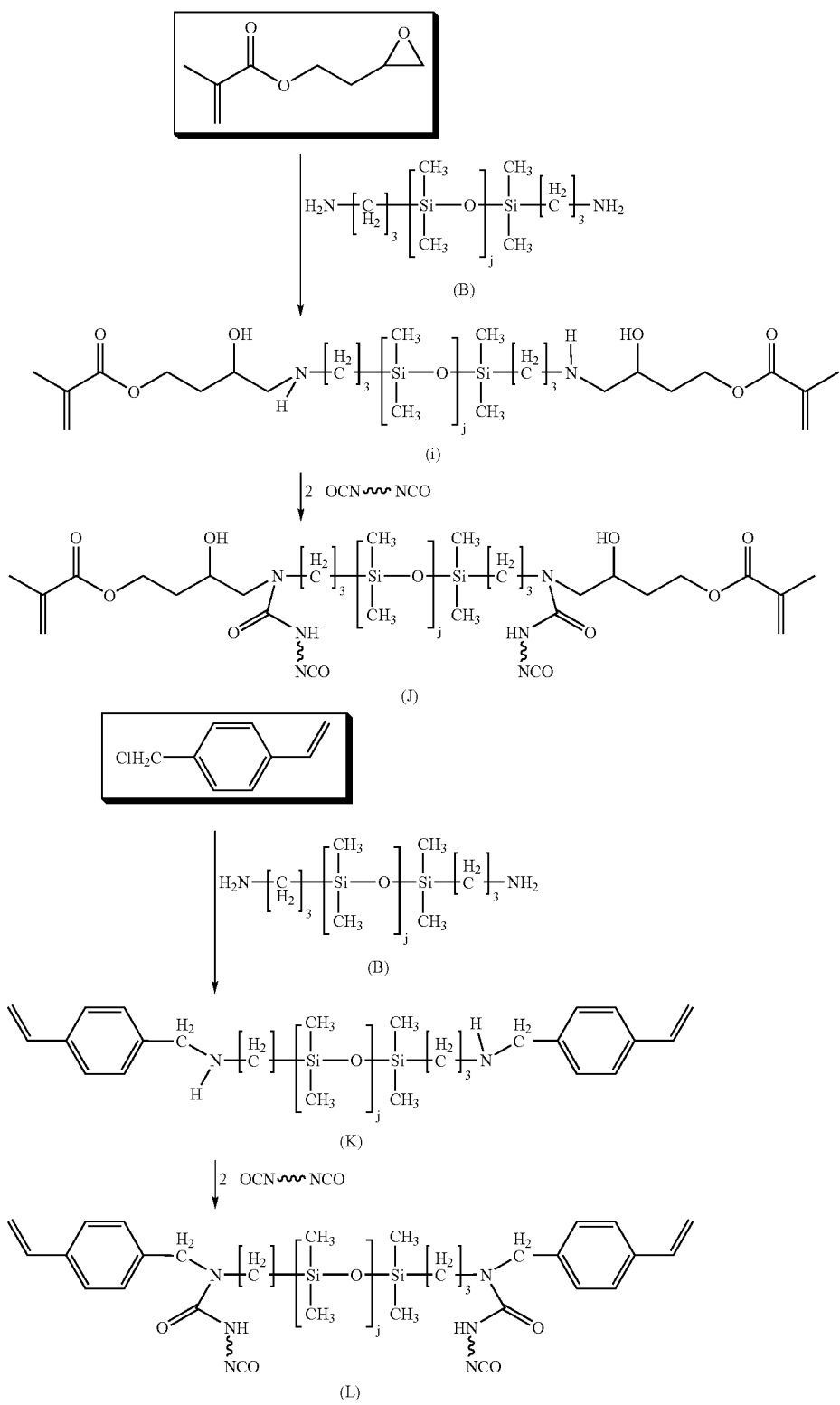

The following examples illustrate the working of the present invention.

Starting Materials:

| Material | Code | Supplier |
|---|---|---|
| Pendant amino-functional PDMS (AEW 1170) | AMS 162 | Apollo |
| Terminal amino-functional PDMS (AEW 810) | DMS A12 | Apollo |
| Terminal amino-functional PDMS (AEW 1265) | DMS A15 | Apollo |
| Terminal amino-functional PEG (AEW 315) (Jeffamine ED 600) | JED 600 | Huntsman |
| Ethylene diamine | ED | Aldrich |
| Allyl isocyanate | AI | Aldrich |
| Dimethyl meta-isopropenyl benzyl isocyanate | TMI | Cytec |
| Isophorone diisocyanate | IPDI | Aldrich |
| Hexamethylene diisocyanate | HMDI | Aldrich |
| Meta-tetramethylxylylene diisocyanate | TMXDI | Cytec |
| Vinylpyrollidone | VP | Aldrich |
| Dimethylacrylamide | DMA | Aldrich |
| t-Butylaminoethyl methacrylate | BAM | Aldrich |
| Hydroxyethyl acrylate | HEA | Aldrich |
| Ethylhexyl acrylate | EHA | Aldrich |
| Butyl acrylate | BA | Aldrich |
| Glycidyl methacrylate | GMA | Aldrich |
| Chloromethyl styrene | CMS | Kodak |
| Acryloyl phosphorylcholine | APC | Example 2a |
| Isopropanol | IPA | Romil |
| Acryloxyethyl methacrylate | AEM | Example 12 |

PEG refers to polyethyleneglycol and AEW refers to amine equivalent weight.

EXAMPLE 1

Preparation of a Silicone/HEA/TMI Macromer 30 g of AMS 162 (AEW 1170, Apollo Scientific) was weighed into a 250 ml r.b. flask fitted with stirrer, thermometer and nitrogen blanket. 3.0 g of HEA was added and a small exotherm (~5° C.) was noted. An oil bath was placed around the flask and the temperature raised to 60° C. After 1 h the reaction was cooled to 35° C.

$^1$H NMR confirmed the loss of the HEA acrylate double bond (5.8(d)/6.1(q)/6.4(d)). Peak assignments (Jeol GSX 400, 399.9 MHz, CDCl$_3$, ppm): ~0.1 (Si—C$\underline{H}_3$); 0.45 (Si—C$\underline{H}_2$—); 1.50 (Si—CH$_2$—C$\underline{H}_2$—); 2.55 (combined multiplet, —C$\underline{H}_2$—NH—C$\underline{H}_2$—); 2.87 (—C$\underline{H}_2$—CO—); 3.71 (—C$\underline{H}_2$—OH); 4.22 (—COO—C$\underline{H}_2$—) 8.0 g of DMA (Aldrich) was then added followed by 5.2 g of TMI (Cytec Industries Inc.) with a wash of 1.6 g of DMA. A 20° C. exotherm was noted and the reaction mixture was then heated to 80° C. and held for 1 h. The resulting macromer in DMA solvent was cooled and FT-IR spectroscopy used to show the disappearance of the isocyanate component (intense N=C=O stretch at ~2260 cm$^{-1}$ absent).

Isolation and characterisation of the adduct by $^1$H NMR showed additional peaks due to the TMI moiety (Jeol GSX 400, 399.9 MHz, CDCl$_3$, ppm): 1.59 (s, Ar—C(C$\underline{H}_3$)$_2$—); 2.05 (s, a—C$\underline{H}_3$); 4.90/5.29 (—C(CH$_3$)=C$\underline{H}_2$); 7.19/7.38 (Ar—$\underline{H}$) in addition to some minor peak shifts due to the conversion of the 2° amine to the urea function R$_2$N—CO—NH—.

EXAMPLE 2a

Preparation of APC (2-Acryloyloxyethyl)-2'-(trimethyl-ammoniumethyl) phosphate, inner salt (Acryloyl-phosphorylcholine, APC) was made by a modification of the route described previously by Ishihara et al. (*Polym. J.*, 22(3), 355, 1990):

All glassware was dried thoroughly before use. 2-Chloro-2-oxo 1,3,2 dioxaphospholane (CCP, Avocado Chemical Co.) (68.3 g, 0.48 mol, 1.05 equiv.) was weighed into a 250 ml self-equilibrating dropping funnel and dissolved in ~50 ml of acetonitrile. Hydroxyethyl acrylate (HEA, Aldrich Chemical Co.) (53 g, 0.46 mole) was measured into a 3-neck 2 L r.b. flask, fitted with a thermometer (range –100° C.–50° C.), the dropping funnel, a N$_2$ bubbler and a magnetic stirrer. The HEA was dissolved in 700 ml acetonitrile and cooled to 0° C. using a solvent/CO$_2$ bath. Whilst stirring, N,N,N',N'-tetramethylene diamine (TMEDA, Aldrich Chemical Co.) (36 g, 0.24 mol, 1.05 equiv.) were added, followed by the dropwise addition of the CCP solution over a 20 minute period. The reaction mixture went cloudy upon addition of the CCP as the TMEDA.2HCl salt formed. The reaction was left to stir for 2 hours.

The TMEDA.2HCl was filtered off under vacuum and an N$_2$ atmosphere and washed with acetonitrile (~60 ml). The clear pale yellow solution was collected in a 2 L Florentine flask. A solvent/CO$_2$ bath was used to cool the solution to ~0° C. before bubbling Trimethylamine (TMA, Aldrich Chemical Co.) (81.53, 1.38 mol, 3 equiv.) into the solution, while stirring. The flask was fitted with an air condenser with a balloon attached to the top and stirred at 50° C. for 16 hours. Excess TMA was then removed under vacuum via a solvent/CO$_2$ cold trap, using a HCl trap, whilst stirring at 40° C. ~300 ml of acetonitrile was removed and white solid product of APC was filtered off under vacuum and N$_2$.

Weight of product collected=93.7 g ° 73%. $^1$H NMR (in D$_2$O) confirmed the product had been made (characteristic singlet for —N$^+$(CH$_3$)$_3$ @ 3.15–3.22 ppm, double bond of the acrylate @ 5.98–6.02 ppm (doublet), 6.19–6.26 ppm (quartet), 6.44–6.48 ppm (doublet)). $^{31}$P NMR (in CDCl$_3$) showed a peak @ –0.53 ppm as expected.

EXAMPLE 2b

Preparation of a Silicone/APC/AI Macromer 7.4 g of APC was weighed into a 250 ml r.b. flask fitted with stirrer, thermometer and nitrogen blanket. 18.0 g of iPA solvent was added and the mixture was heated to 60° C. The APC completely dissolved at about 50° C. 30 g of AMS 162 was added with a wash of a further 7.0 g of iPA. The temperature was held at 60° C. for 15 min and then raised to reflux (ca. 80° C.). After 1 h the reaction was cooled to 40° C. and 2.1 g of allyl isocyanate (Aldrich) added with a wash of 1.4 g of iPA. An exotherm was noted and the mixture was heated to reflux for 1 h. After cooling, FT-IR spectroscopy confirmed the reaction of all isocyanate by loss of the N=C=O stretch.

Removal of the solvent under vacuum to yield a thick gum and subsequent $^1$H NMR analysis of this product confirmed the expected structure for the adduct (Jeol GSX 400, 399.9 MHz, CDCl$_3$, ppm): ~0.1 (Si—C$\underline{H}_3$); 0.46 (Si—C$\underline{H}_2$—); 1.57 (Si—CH$_2$—C$\underline{H}_2$—); 2.59 (—C$\underline{H}_2$—COO—); 3.08 (b, C$\underline{H}_2$—N—C$\underline{H}_2$ & CONH—C$\underline{H}_2$—); 3.30 (N$^+$(CH$_3$)$_3$); 3.49/3.8/4.1/4.25 (—COOC$\underline{H}_2$C$\underline{H}_2$OP(OO—)OC$\underline{H}_2$C$\underline{H}_2$—N—); 4.22 (—COO—C$\underline{H}_2$—); 5.05/5.15/5.87 (allyl-C$\underline{H}$=C$\underline{H}_2$)

EXAMPLES 3–10

Preparation of Macromers Based on AMS 162

Following the procedures outlined in examples 1 and 2, the macromers shown in Table 1 were similarly prepared using AMS 162 as the amino-silicone:

TABLE 1

Silicone Macromers based on AMS 162

| Example # | a,b-Unsat. Compound | Isocyanate | Solvent |
|---|---|---|---|
| 3 | HEA | TMI | iPA |
| 4 | HEA | AI | DMA |
| 5 | APC | TMI | IPA |
| 6 | EHA | TMI | IPA |
| 7 | HEA, APC | TMI | DMA |
| 8 | APC | TMI | HEMA |
| 9 | HEA | TMI | HEMA |
| 10 | HEA | TMI | VP |

EXAMPLE 11

Preparation of a Silicone/HEA-IPDI-BAM Macromer 60.0 g of DMS A12 (AEW 810, Apollo Scientific) was weighed into a 250 ml r.b. flask fitted with stirrer, thermometer and nitrogen blanket. 8.6 g of HEA was added at 17° C. and an exotherm to 35° C. was observed. The temperature was raised to 60° C. and held for 1 h after which time $^1$H NMR showed complete loss of the acrylate double bond and peak assignments for the product were much the same as described for the pendant amino-PDMS in example 1, demonstrating Michael-type addition of the acrylate to amine.

The reaction mixture was cooled and 13.8 g of t-butylaminoethyl methacrylate (BAM) was added followed by 20.0 g of N,N dimethylacrylamide (DMA) wash and diluent. 15.7 g of isophorone diisocyanate was added at 30° C. followed by 4.5 g of DMA wash. The reaction was held at 60° C. for a further 1 h and FT-IR spectroscopy used to show complete reaction of the isocyanate groups (disappearance of the N=C=O stretch at 2258 cm$^{-1}$).

EXAMPLE 12

Preparation of a Silicone/APC-JED600/APC-TMXDI-BAM Macromer 5.62 g of APC was weighed into a 250 ml r.b. flask fitted with stirrer, thermometer and nitrogen blanket. 12.0 g of iPA was added and the mixture heated to 60° C. to dissolve the APC. When a clear solution was obtained a blend of 3.15 g of Jeffamine ED600 and 12.65 g of DMS A15 in 6.0 g of iPA was added. The mixture was heated at reflux for 90 min after which it was cooled and 1.85 g of BAM added at 40° C. 3.65 g of TMXDI was then added. The mixture exothermed and was held at reflux for 1 h. IR spectroscopy showed no isocyanate to be present.

EXAMPLE 13a

Synthesis of Acryloyloxyethyl Methacrylate (AEM)

5.0 g of hydroxyethyl methacrylate was weighed into a 250 ml r.b. flask fitted with stirrer, thermometer and nitrogen blanket. 3.88 g of triethylamine was then added followed by 80 ml of dichloromethane. The mixture was cooled and 4.15 g of acryloylchloride was added dropwise. The reaction mixture turned yellow and after 10 min a precipitate formed. Stirring was continued for 90 minutes. The precipitated material (TMEDA.HCl) was then filtered off and the organic solution extracted with sodium bicarbonate solution. The solution was then dried over anhydrous magnesium sulphate and after filtration the solvent evaporated to give a pale yellow oil (yield~90%).

$^1$H NMR confirms the structure expected for AEM (Jeol GSX 400, 399.9 MHz, CDCl$_3$, ppm): 1.95 (3H, s, C$\underline{H}_3$—); 4.40 (4H, m, —COO—CH$_2$CH$_2$—OOC—); 5.31/5.70 (1H each, s, (CH$_3$)C=C$\underline{H}_2$); 5.87(d)/6.13(q)/6.45(d) (C$\underline{H}_2$=C$\underline{H}$—)

EXAMPLE 13b

Preparation of a Silicone/AEM-JED600-IPDI-BAM Macromer 16.4 g of DMS A12 was weighed into a 100 ml r.b. flask fitted with stirrer, thermometer and nitrogen blanket. 3.6 g of AEM were added with stirring and the reaction mixture heated to 80° C. for 1 h. After this time $^1$H NMR showed the complete reaction of the acrylate functionality (multiplets from 5.87–6.45 disappear), whilst the methacrylate groups were intact (two singlets at 5.30 & 5.71 ppm).

6.3 g of Jeffamine ED600 and 3.7 g of BAM in 10.0 g of iPA were then added with 5.0 g of iPA rinse. After stirring for a few minutes 6.6 g of isophorone diisocyanate was added with 3.0 g of iPA rinse. After the exotherm the reaction mix was heated to 80° C. for 1 h . IR spectroscopy showed no isocyanate present (no N=C=O stretch at 2258 cm$^{-1}$).

EXAMPLE 14

Preparation of a Silicone/GMA-IPDI-BAM Macromer 16.4 g of DMS A12 was weighed into a 100 ml r.b. flask fitted with stirrer, thermometer and nitrogen blanket. 2.8 g of glycidyl methacrylate was added and the mixture heated for a minimum of 2 h.

7.0 g of iPA was then added and the mixture cooled to 40° C. 3.7 g of BAM were added, followed by 4.4 g of isophorone diisocyanate and a wash of 6.4 g iPA. The mixture was heated at reflux for 1 h after which time IR spectroscopy showed no isocyanate to be present.

EXAMPLE 15

Preparation of a Silicone/HEA/CMS Macromer 11.7 g of AMS 162 was weighed into a 100 ml r.b. flask fitted with stirrer, thermometer and nitrogen blanket. 1.16 g of HEA was added to this and the mixture heated for 1 h at 60° C. $^1$H NMR confirmed the Michael-type addition of the acrylate to the amine as described for example 1.

After this time, 1.56 g of chloromethylstyrene (CMS, Kodak Chemicals) was added and the mixture heated for several hours with nitrogen bubbling through the mixture to ensure degassing of any HCl formed upon reaction. After this time a thick gum was isolated and was shown by $^1$H NMR to have CMS extensively reacted at the 2° amine positions of the adduct:

(Jeol GSX 400, 399.9 MHz, CDCl$_3$, ppm): ~0.1 (Si—C$\underline{H}_3$); 0.45 (Si—C$\underline{H}_2$—); 1.50 (Si—C$\underline{H}_2$—C$\underline{H}_2$—); 2.55 (combined multiplet, —C$\underline{H}_2$—NR—C$\underline{H}_2$—); 2.80 (—C$\underline{H}_2$—CO—); 3.61 (Ar—C$\underline{H}_2$—N—); 3.71 (—C$\underline{H}_2$—OH); 4.22 (—COO—C$\underline{H}_2$—); 5.2(d)/5.75(d) (ArC$\underline{H}$=C$\underline{H}_2$); 6.7 (m)/7.35(m) (Ar—$\underline{H}$)

EXAMPLES 16–28

Silicone Macromers Based on DMS A12

Following the procedures outlined in examples 11–13, the macromers in Table 2 were similarly prepared:

TABLE 2

Silicone Macromers Based on DMS A12

| Example # | Other Diamine | a,b-Unsat. Compound | Isocyanate | Capping Group | Solvent |
|---|---|---|---|---|---|
| 16 | — | HEA | TMXDI | BAM | iPA |
| 17 | — | APC | TMXDI | BAM | iPA |
| 18 | — | HEA | TMXDI | BAM | iPA |
| 19 | — | EHA | TMXDI | BAM | iPA |
| 20 | — | APC | HMDI | HEMA | Hexanol |
| 21 | JED 600 | HEA | TMXDI | BAM | iPA |
| 22 | JED 600 | HEA | IPDI | BAM | iPA |
| 23 | JED 600 | HEA | HMDI | BAM | iPA |
| 24 | JED 600 | BA | TMXDI | BAM | iPA |
| 25 | JED 600 | BZA | TMXDI | BAM | iPA |
| 26 | JED 600 | APC | TMXDI | BAM | iPA |
| 27 | ED | APC | TMXDI | BAM | IPA/Hexanol |
| 28 | JED 600 | GMA | IPDA | BAM | iPA |

EXAMPLE 29

Generic Method for Conact Lens Preparation and Evaluation

The contact lens formulation (macromer/comonomers/initiator/crosslinker) was placed into a glass vial and the mixture degasssed for 10 mins with N$_2$ before dispensing known amounts into polypropylene contact lens moulds (to give −3.0 D power lenses). The moulds were then sealed and UV cured for 1 hour using a Blak-Ray longwave UV lamp model B100AP. The lenses were removed from the mould by soaking in high purity water for 1 hour. They were then soaked in a 70:30 water IPA solution for 2 hours and in borate buffered saline for a further hour. The lenses were then bottled in buffer. A visual assessment of the lenses was made and this was recorded.

Lenses were placed in vials that were filled with buffer solution. They were then sterilised by autoclaving at 120° C. for 30 mins. A visual assessment of the lenses was made and this was recorded.

The equilibrium water content (EWC) of the lens was determined by firstly removing excess (free) water from the lens surface by use of filter paper. The lenses were then placed on a pyrex dish containing drierite and microwaved for 5 minutes on full power (800 watts) and reweighed. The EWC was then calculated as follows:

EWC (%)=hydrated weight of lens-dry weight of lens×100% hydrated weight of lens

The oxygen permeability (Dk) of the lenses was determined by use of Mocon's OptiPerm™ technology according to their SOP#70-006, designed for measuring the Dk value of hydrophilic contact lens materials (Mocon/Modern Controls Inc., 7500 Boone Avenue North, Minneapolis, Minn., 55428 USA).

EXAMPLES 30–35

Contact Lens Formulations Using Invention Macromers

Contact lens formulations were on the basis of mixing the macromers of the described invention with NNDMA for further water content enhancement, TRIS for extra silicone content and increase O$_2$ permeability, EGDMA cross-linked for mechanical properties and Darocur as the UV initiator (see Table 3 for typical formulations).

TABLE 3

Typical Contact Lens Formulations Using Macromers of the Invention

| Ex. # | Macromer Example # | Macromer (g) | NNDMA (g) | TRIS (g) | EGDMA (g) | Darocur (g) |
|---|---|---|---|---|---|---|
| 30 | 3 | 2.0625 | 2.0536 | 1.2559 | 0.0581 | 0.0519 |
| 31 | 11 | 4.0624 | 0.4235 | 0.5225 | 0.0503 | 0.0529 |
| 32 | 11 | 3.2616 | 1.0325 | 0.6629 | 0.0524 | 0.0550 |
| 33 | 11 | 5.0143 | 1.0314 | 1.0123 | 0.0752 | 0.0753 |
| 34 | 17 | 1.8291 | 0.7503 | 0.5773 | 0.0532 | 0.0311 |
| 35 | 23 | 5.447 | 0.7604 | 0.6109 | 0.0471 | 0.0585 |

After polymerisation as described in example 29, lenses with the properties described in Table 4 were obtained (n=5 for data):

TABLE 4

Properties of Lenses Made Using Macromers of the Invention

| Example # | Appearance (post UV cure) | Appearance (post autoclave) | EWC (%) | Dk × 10$^{10}$ (ccO$_2$/cm$^2$sec mmHg) |
|---|---|---|---|---|
| 30 | Clear, colourless | Clear, colourless | 33 | * |
| 31 | Clear, colourless | Clear, colourless | 18 | 99.0 |
| 32 | Clear, colourless | Clear, colourless | 30 | 92.1 |
| 33 | Clear, colourless | Clear, colourless | 25 | 101.6 |
| 34 | Clear, colourless | Clear, colourless | 31 | 81.9 |
| 35 | Clear, slight yellow | Clear, slight yellow | 54 | (awaiting) |

(* = Not tested for Dk)

BRIEF DESCRIPTION OF THE DRAWINGS

Selected silicone lenses were tested for their water permeability and compared to a conventional PHEMA membrane, PHEMA lenses and a commercially available silicone hydrogel lens. The water permeability was determined using a method that employs the use of tritiated water on one side of the lens and its subsequent detection on the other side of the lens allows the relative water permeability to be measured (FIG. 1).

The water permeabilities are seen to be superior to PHEMA hydrogels and indeed better than commerically available silicone hydrogel materials.

Figure 1:
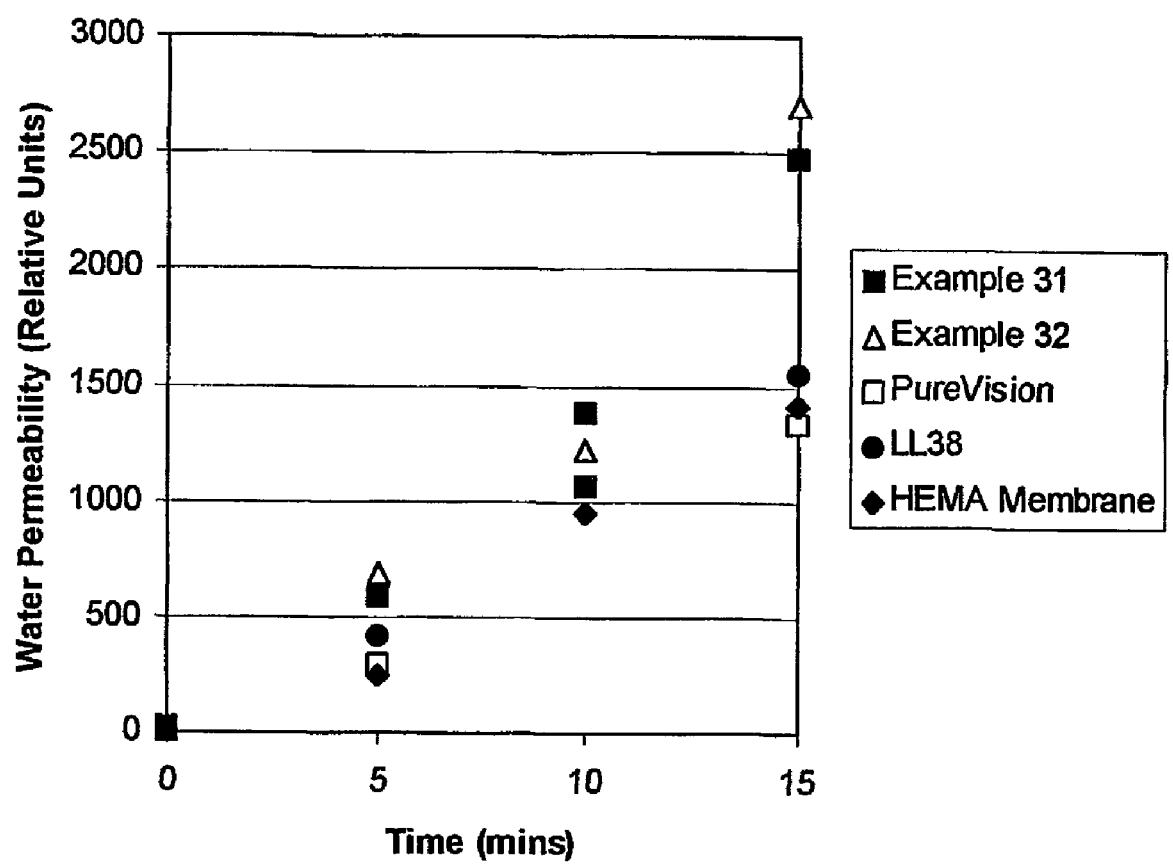

The invention claimed is:

1. A silicon containing adduct having the formula (X)

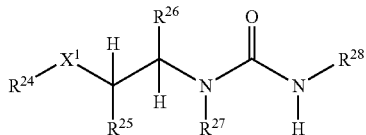

(X)

in which $X^1$ is an electron withdrawing group selected from the group consisting of carbonyl and sulphone groups, suiphonium and phosphonium salts;

$R^{24}$ is a zwitterion or hydroxy substituted alkoxy, alkoxy alkoxy or oligoalkoxy alkoxy group;

$R^{25}$ and $R^{26}$ are independently selected from hydrogen and $C_1$–$C_{12}$ alkyl groups;

$R^{27}$ is a group of formula VII

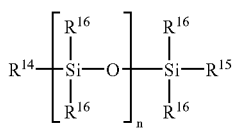

(VII)

in which $R^{14}$, $R^{15}$ and each $R^{16}$ are independently selected from monovalent groups selected from hydrogen, branched and straight $C_{1-12}$ alkyl, $C_{6-18}$ aryl, $C_{6-18}$ alkaryl, $C_{6-18}$ aralkyl, $C_{2-12}$ alkenyl, $C_{2-12}$ alkynyl and $(-OSiR^{16}_2)_p$ $OSiR^{16}_3$, and divalent groups selected from branched and straight $C_{1-12}$-alkanediyl, $C_{6-18}$-arylene, $C_{7-18}$-alkarylene, $C_{12-2}$-alkenediyl and $C_{12-2}$-alkynediyl, any of which may be substituted by a primary, secondary or tertiary amine group and/or a group $X^1CH(R^{25})CH(R^{26})NR^{27}CONHR^{28}$ or a group $-N(R^{27})CH(R^{26})CH(R^{25})X^1R^{24}$ n is 0–300 and, p is 0 to 50, provided that at least one of the groups $R^{14}$, $R^{15}$ and $R^{16}$ is a divalent radical which is covalently bonded to the nitrogen; and $R^{28}$ is an optionally substituted alkyl, alkenyl, alkynyl, aryl, cycloalkyl, cycloalkenyl or cycloalkynyl group comprising an ethylenically unsaturated or isocyanate group.

2. An adduct according to claim 1, wherein $R^{24}$ includes a zwitterionic group Z, which has the general formula (II)

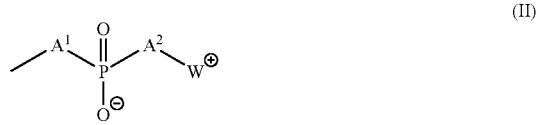

(II)

in which the moieties $A^1$ and $A^2$, which are the same or different, are —O—, —S—, —NH— or a valence bond, and $W^+$ is a group comprising an ammonium, phosphonium or sulphonium cationic group and a group linking the anionic and cationic moieties.

3. An adduct according to claim 2, wherein the zwitterionic group of the formula (II), has the general formula (III):

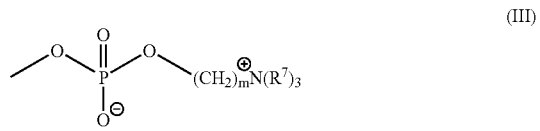

(III)

in which the groups $R^7$ are the same or different and each is hydrogen or $C_{1-4}$ alkyl, and m is from 1 to 4.

4. An adduct according to claim 1, wherein X is a carbonyl group.

5. An adduct according to claim 4, wherein $R^{24}$ is selected from the group consisting of hydroxyalkoxy, hydroxy and poly(oxyalkyl)oxy groups.

6. An adduct according to claim 1, in which $R^{28}$ comprises an ethylenically unsaturated group.

7. An adduct according to claim 1, which has formula (XI) or (XII);

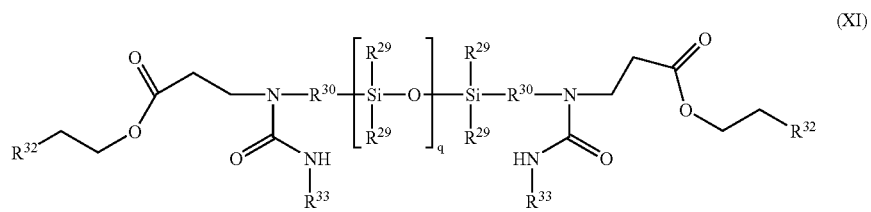

(XI)

-continued

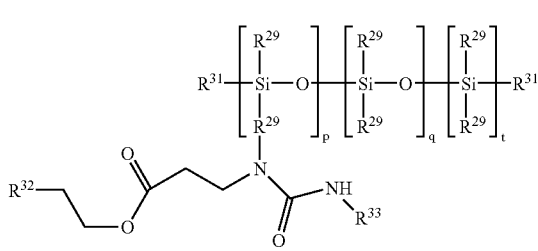

(XII)

wherein
- each group $R^{29}$ and each group $R^{31}$ is independently selected from the group consisting of hydrogen, $C_{1-6}$ alkyl, $C_{6-18}$ aryl, $C_{6-18}$ aralkyl, $C_{6-18}$ alkaryl, and $C_{2-6}$ alkenyl;
- each group $R^{30}$ is independently selected from the group consisting of $C_{1-6}$ alkanediyl, $C_{2-6}$ alkendiyl and $C_{2-6}$ alkynediyl;
- each group $R^{32}$ is selected from the group consisting of hydroxyl, hydroxyalkoxy, hydroxy(oligoalkoxy) and a zwitterionic group Z provided at least one such group is a zwittenonic group Z;
- each group $R^{33}$ is individually selected from the group consisting of linear and branched alkyl, aryl, alkenyl, and alkynyl groups, cycloalkyl, cycloalkenyl, cycloalkynyl, aralkyl, alkaryl, alkoxyaryl, alkoxyalkyl, oligoalkoxyalkyl, arylaminoalkyl, N-aryl-N-alkylaminoalkyl, acyloxyalkyl (including alkenoyloxyalkyl), acylaminoalkyl, acylaminocycloalkyl, acylaminoaryl, N,N-diacyl-iminoalkyl groups, provided that at least one of the groups $R^{33}$ comprises an ethylenically unsubstituted group or an isocyanate group;
- p is an integer of 1 to 50;
- q is an integer of 1 to 500; and
- t is 0 or 1.

8. An adduct according to claim 7, wherein all groups $R^{29}$ and any groups $R^{31}$ are methyl and $R^{30}$ is selected from ethanediyl, propanediyl and butanediyl.

9. Method in which:
i) in a first step a primary amine compound $R^{38}$ $NH_2$ which is an amino-functional organosiloxane compound of the formula (XXI)

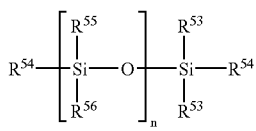

(XXI)

in which $R^{53}$–$R^{56}$ are each selected from $C_{1-12}$ alkyl, $C_{2-12}$ alkenyl and $C_{2-12}$ alkynyl, $C_{6-8}$ aryl, $C_{7-18}$ aralkyl and $C_{7-18}$ alkaryl, any of which may be substituted by a primary amine group, and n is 0–300, provided that at least one of the groups $R^{53}$ to $R^{56}$ is substituted by a primary amine group, is reacted with Michael reagent of the formula $CH(R^{39})$ =$CH(R^{40})X^2R^{41}$ in which $R^{39}$ and $R^{40}$ are independently selected from hydrogen and $C_{1-12}$ alkyl groups, $X^2$ is an electron withdrawing group selected from the group consisting of carbonyl and sulphone groups, sulphonium and phosphonium salts; and $R^{41}$ is selected from linear and branched alkyl, alkenyl, and alkynyl groups, aryl, alkoxycarbonyl, alkylaminocarbonyl, cycloalkyl, cycloalkenyl, cycloalkynyl, haloaryl, haloalkyl, alkaryl, aralkyl, alkoxyaryl, alkoxyalkyl, oligoalkoxyalkyl, aminoalkyl, mono- and di-alkylaminoalkyl, arylaminoalkyl, N-aryl-N-alkylaminoalkyl and -aminoaryl, acyloxy, acyloxyalkyl, acylaminoalkyl, N-diacyl-iminoalkyl groups, alkylaminocarbonyl, oxacycloalkyl, oxacycloalkenyl, organosilane and organosiloxane groups and any of the above groups substituted with a zwitterionic group Z, an isocyanate group, a hydroxyl group or a polymerisable ethylenically unsaturated group to form a secondary amine intermediate $R^{38}$ $NHCH(R^{39})CH(R^{40})X^2R^{41}$, and
ii) in a second step the secondary amine intermediate is reacted with an isocyanate compound $R^{42}$ NCO which reacts at the nitrogen atom of the secondary amine group to form a ureido bond, in which $R^{42}$ is an alkyl, aryl, alkaryl or aralkyl group optionally substituted by an isocyanate or an ethylenically unsaturated group.

10. The method according to claim 9, wherein $R^{39}$ and $R^{40}$ are selected from hydrogen or $C_1$–$C_4$ alkyl groups.

11. The method according to claim 9, in which $X^2$ is carbonyl.

12. A method according to claim 9, wherein each $R^{54}$ is an amino-$C_{1-6}$-alkyl group.

13. The method according to claim 12 in which each $R^{54}$ is aminomethyl, aminoethyl, aminopropyl or aminobutyl.

14. A method according to claim 9, wherein the isocyanate compound has the formula $R^{51}$ $(NCO)_m$, where $R^{51}$ is an in-functional organic radical where m is an integer of 1–10.

15. A method according to claim 13 in which m is 2.

16. The method according to claim 13, wherein the isocyanate compound is selected from the group consisting of $C_{2-30}$ aliphatic, $C_{6-30}$ aromatic and $C_{6-20}$ alicyclic diisocyanates, $C_{4-30}$ allyl isocyanates, $C_{4-30}$ isocyanatoalkylacrylates and $C_{5-30}$ isocyanato alkylmethacrylates.

17. The method according to claim 9, wherein the reaction is carried out in a solventless system.

18. The method according to claim 9, wherein the reaction is carried out in the presence of a solvent selected from $C_{1-8}$ alcohols, $C_{1-8}$ chlorinated hydrocarbons $C_{1-8}$ alkylacrylamides and $C_{1-8}$ ethers, preferably selected from secondary $C_{1-8}$ and tertiary alcohols.

19. The method according to claim 18, wherein the alcohol is selected from isopropanol, isobutanol, tertbutanol hydroxyalkyl(meth)acrylate.

20. A composition comprising an admixture of an adduct according to claim 6, with ethylenically unsaturated comonomers.

21. A composition comprising a polymer produced by polymerisation of an admixture according to claim 20.

22. A composition according to claim 21, which is a liquid composition comprising a solvent in which the polymer is dissolved or suspended.

23. An article produced from or coated by an adduct according to claim 9.

24. An article according to claim 23, wherein the article is a contact lens.

25. A polymer produced by the homo-polymerisation or co-polymerisation of an adduct according to claim 1.

26. A polymer according to claim 25, which is produced from an adduct according to claim 6 by a polymerisation process selected from free radical, cationic, anionic and metal catalysed polymerisations.

27. A process for coating a surface comprising applying a composition according to claim 22 to the surface of a polymer or metal and substantially removing the solvent.

28. A polymerisation process comprising the homo-polymerisation or co-polymerisation of an adduct according to claim 1.

29. An adduct according to claim 2, wherein $W^+$ is a group of formula $—W^1—N^+R^5_3$, $—W^1—P^+R^6_3$, $—W^1—S^+R^6_2$ or $—W^1$-Het$^+$ in which:

$W^1$ is alkanediyl of 1 or more, preferably 2–6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^5$ are the same or different and each is hydrogen or alkyl of 1 to 4 carbon atoms, or two of the groups $R^5$ together with the nitrogen atom to which they are attached form an aliphatic heterocyclic ring containing from 5 to 7 atoms, or the three groups $R^5$ together with the nitrogen atom to which they are attached form a fused ring structure containing from 5 to 7 atoms in each ring, and optionally one or more of the groups $R^5$ is substituted by a hydrophilic functional group, and the groups are the same or different and each is $R^5$ a group $OR^5$, where $R^5$ as defined above; or Het is an aromatic nitrogen-, phosphorus- or sulphur-containing ring, for example pyridine.

* * * * *